(12) United States Patent
Qiao et al.

(10) Patent No.: US 12,285,289 B2
(45) Date of Patent: Apr. 29, 2025

(54) MODULAR ULTRASOUND APPARATUS AND METHODS

(71) Applicant: Orthoson Limited, Oxford (GB)

(72) Inventors: Shan Qiao, Headington (GB); Delphine Elbes, Headington (GB); Olga Boubriak, Headington (GB); Robin Cleveland, Headington (GB); Constantin Coussios, Headington (GB)

(73) Assignee: ORTHOSON LIMITED, Oxford (GB)

( * ) Notice: Subject to any disclaimer, the term of this patent is extended or adjusted under 35 U.S.C. 154(b) by 271 days.

(21) Appl. No.: 16/341,240

(22) PCT Filed: Oct. 9, 2017

(86) PCT No.: PCT/GB2017/053045
§ 371 (c)(1),
(2) Date: Apr. 11, 2019

(87) PCT Pub. No.: WO2018/069684
PCT Pub. Date: Apr. 19, 2018

(65) Prior Publication Data
US 2020/0037990 A1    Feb. 6, 2020

(30) Foreign Application Priority Data

Oct. 11, 2016 (GB) .................................... 1617255

(51) Int. Cl.
*A61B 8/00*   (2006.01)
*A61N 7/00*   (2006.01)

(52) U.S. Cl.
CPC .......... *A61B 8/4411* (2013.01); *A61B 8/4494* (2013.01); *A61B 8/463* (2013.01);
(Continued)

(58) Field of Classification Search
CPC ....... A61B 8/4411; A61B 8/4494; A61B 8/42; A61N 7/00; A61N 2007/0052; A61N 2007/0065; A61N 2007/0078
See application file for complete search history.

(56) References Cited

U.S. PATENT DOCUMENTS 6,497,665 B1   12/2002   Hunt et al.
8,545,405 B2   10/2013   Raghavan et al.
(Continued)

FOREIGN PATENT DOCUMENTS

CN   1494933 A   5/2004
CN   1890031 A   1/2007
(Continued)

OTHER PUBLICATIONS

International Preliminary Report on Patentability mailed Apr. 25, 2019, issued in International Application No. PCT/GB2017/053045, 10 pages.
(Continued)

*Primary Examiner* — Pascal M Bui Pho
*Assistant Examiner* — Neshat Baset
(74) *Attorney, Agent, or Firm* — Wegman Hessler Valore

(57) ABSTRACT

A pressure wave system comprises a plurality of modules (200). Each module (200) comprises a plurality of pressure wave transducer elements, and connection means (216, 218, 220) operable to connect the modules together in each of a plurality of different configurations. The modules can form a transmitter array having a plurality of different shapes each associated with one of the configurations.

11 Claims, 16 Drawing Sheets

(52) U.S. Cl.
CPC ............... *A61B 8/466* (2013.01); *A61N 7/00* (2013.01); *A61B 8/42* (2013.01); *A61N 2007/0052* (2013.01); *A61N 2007/0065* (2013.01); *A61N 2007/0078* (2013.01)

(56) References Cited

U.S. PATENT DOCUMENTS

| | | | |
|---|---|---|---|
| 2004/0122323 A1* | 6/2004 | Vortman | A61N 7/02 600/459 |
| 2005/0154314 A1* | 7/2005 | Quistgaard | A61N 7/02 600/459 |
| 2010/0030076 A1* | 2/2010 | Vortman | A61N 7/02 600/439 |
| 2011/0071397 A1* | 3/2011 | Wodnicki | B06B 1/0629 600/459 |
| 2012/0165670 A1 | 6/2012 | Shi et al. | |
| 2013/0178764 A1 | 7/2013 | Eckhouse et al. | |
| 2013/0289593 A1 | 10/2013 | Hall | |
| 2014/0058297 A1* | 2/2014 | Clark | A61N 7/02 601/3 |
| 2015/0032002 A1* | 1/2015 | Rothberg | A61B 8/4483 600/440 |
| 2016/0187473 A1* | 6/2016 | Maev | A61B 8/0808 600/442 |
| 2018/0249986 A1* | 9/2018 | Lee | A61B 8/145 |

FOREIGN PATENT DOCUMENTS

| | | |
|---|---|---|
| CN | 102218394 A | 10/2011 |
| CN | 103220981 A | 7/2013 |
| CN | 203724652 U | 7/2014 |
| CN | 103969651 A | 8/2014 |
| CN | 104367340 A | 2/2015 |
| CN | 104936516 A | 9/2015 |
| CN | 104936517 A | 9/2015 |
| CN | 105530869 A | 4/2016 |
| DE | 10215416 A1 | 10/2003 |
| EP | 1259166 A1 | 11/2002 |
| EP | 1345527 A2 | 9/2003 |
| WO | WO-0078232 A1 * | 12/2000 ............... A61N 7/02 |
| WO | 2007062267 A2 | 5/2007 |
| WO | 2008137942 A1 | 11/2008 |
| WO | 2008143998 A1 | 11/2008 |
| WO | 2012131383 A1 | 4/2012 |
| WO | 2014031142 A1 | 2/2014 |
| WO | WO-2014164363 A1 * | 10/2014 ............. A61B 8/085 |

OTHER PUBLICATIONS

International Search Report and Written Opinion dated Dec. 13, 2017, in International Application No. PCT/GB/2017/053045, 14 pages.

Search Report dated Mar. 21, 2017, in Application No. GB 1617255. 3, 6 pages.

Search Report issued in Chinese Patent Application No. CN2017800748885 dated Oct. 19, 2020; 16 pages.

Ter Harr et al., "High Intensity focused ultrasound: Physical principles and devices", International Journal of Hyperthermia, Mar. 2007; pp. 89-104.

De Saint Victor et al., "Properties, characteristics and applications of microbubbles for sonothrombolysis", informa healthcare, University of Oxford Institute of Biomedical Engineering, Expert Opinion, 2013, pp. 1-23.

Mo et al., "Ultrasound-enhanced drug delivery for cancer", informa healthcare, University of Oxford Department of Oncology, Expert Opinion, 2012, pp. 1525-1538.

Hynynen, PhD et al., "Noninvasive MR Imaging—guided Focal Opening of the Blood-Brain Barrier in Rabbits", Experimental Studies, Department of Radiology, Brigham and Women's Hospital, Harvard Medical School, Aug. 21, 2001, pp. 640-646.

Elias, M.D., et al., "A Pilot Study of Focused Ultrasound Thalamotomy for Essential Tremor", The New England Journal of Medicine, 2013, pp. 640-648.

Nau, PhD et al., "Intradiscal Thermal Therapy Using Interstitial Ultrasound", SPINE vol. 32, No. 5, pp. 503-511, 2007.

Weeks et al., "MRI-guided focused ultrasound (MRgFUS) to treat facet joint osteoarthritis low back pain—case series of an innovative new technique" European Society of Radiology (2012) pp. 2822-2835.

* cited by examiner

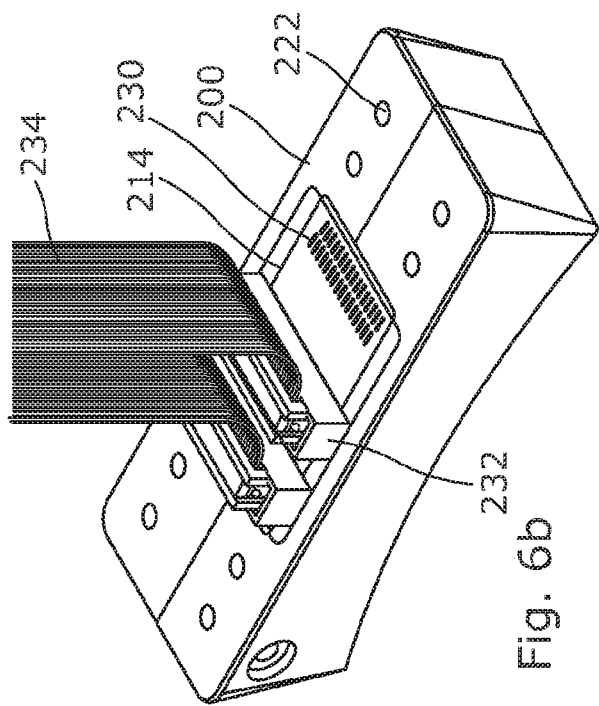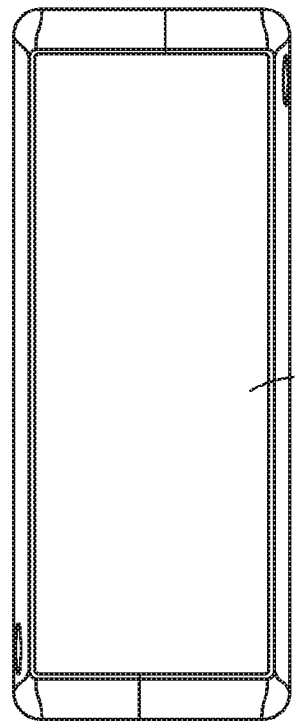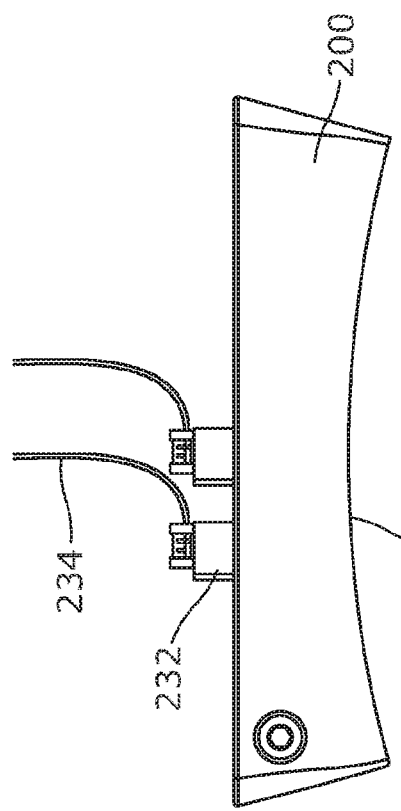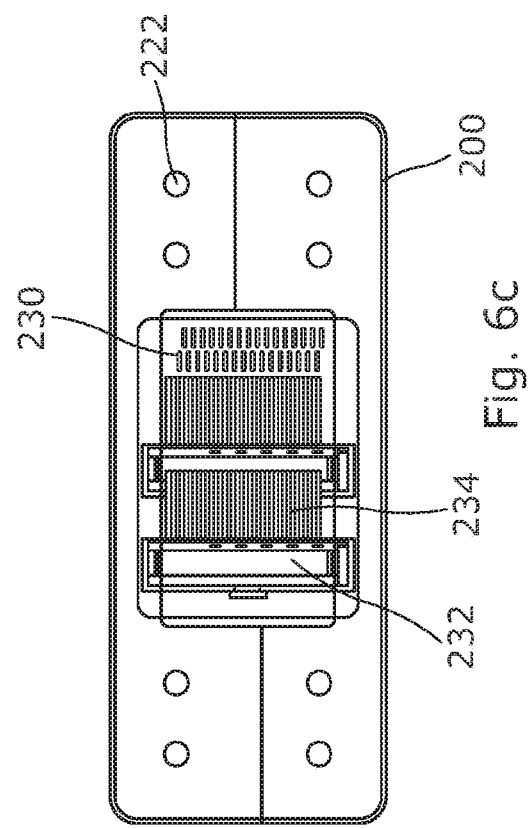

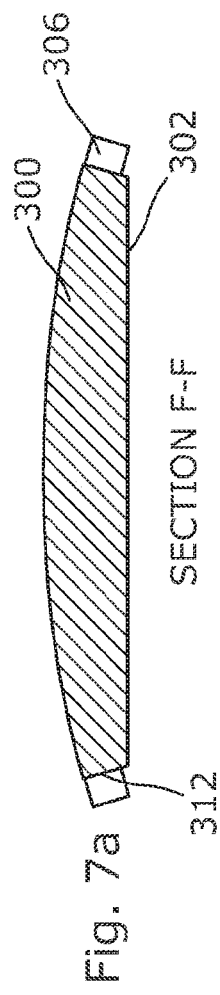
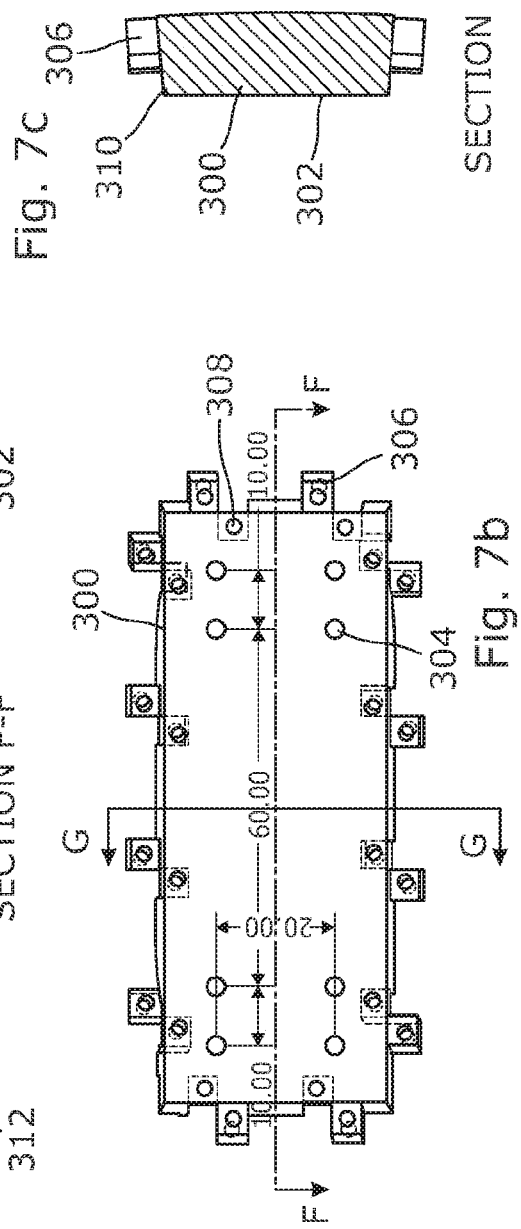
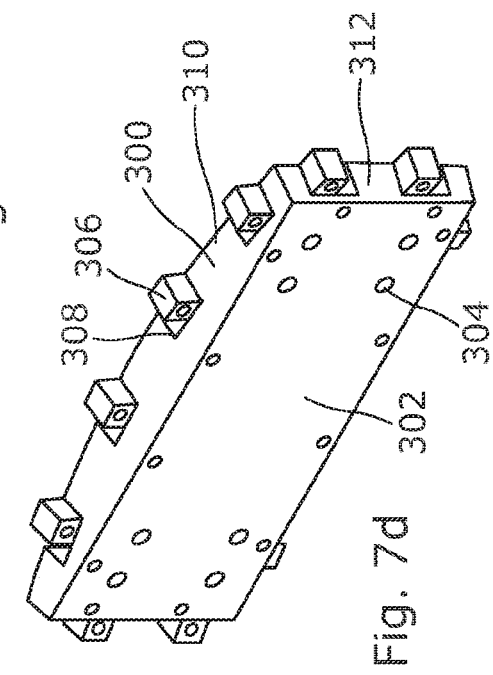

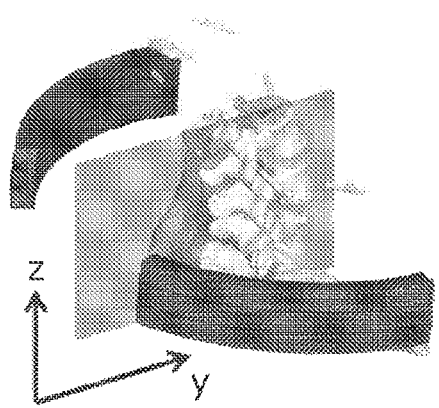
Fig. 17a
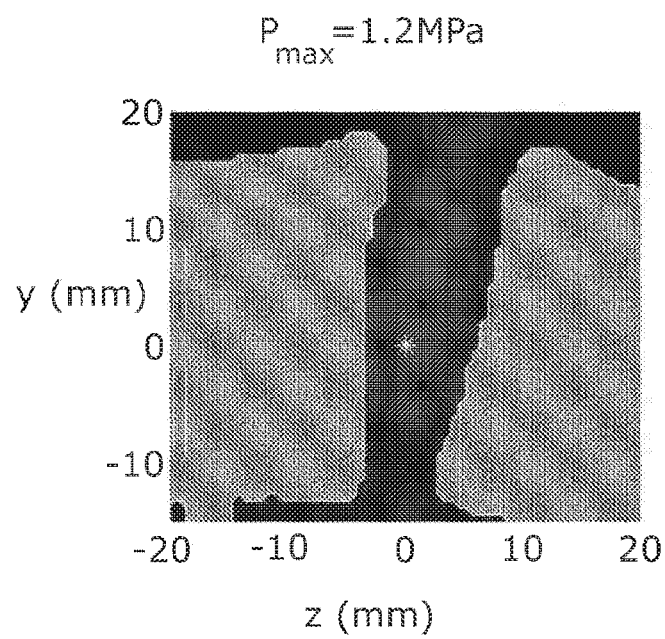
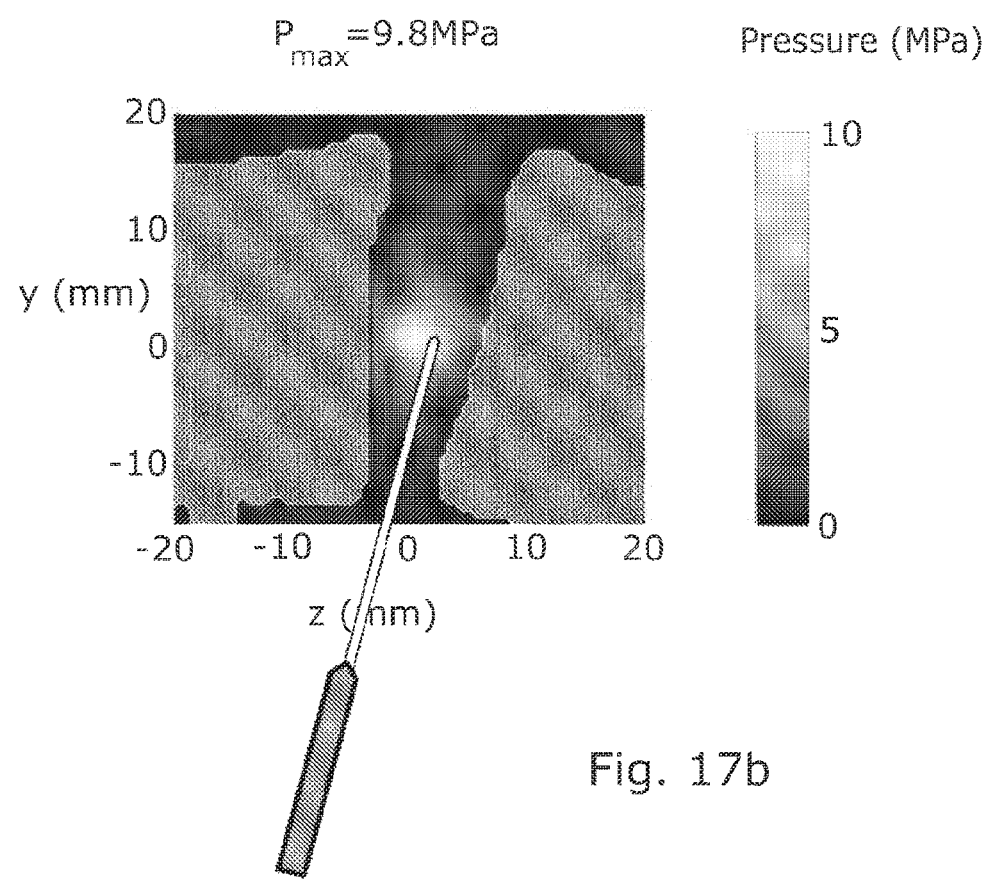
Fig. 17b

MODULAR ULTRASOUND APPARATUS AND METHODS

CROSS REFERENCE TO RELATED APPLICATION

This application is a national phase of International Patent Application No. PCT/GB2017/053045 filed Oct. 9, 2017, which claims the priority filing benefit of United Kingdom Patent Application No. GB1617255.3 filed Oct. 11, 2016, and which are incorporated herein by reference in their entirety.

FIELD OF THE INVENTION

The present invention relates to ultrasound systems, and in particular medical ultrasound systems for imaging, diagnosis and therapy. In particular it has application in focussed ultrasound (FUS) and high intensity focussed ultrasound (HIFU) treatment, as well as conventional diagnostic ultrasound imaging, of areas where acoustic access is difficult or complex due to the presence of bone or air, for example of the intervertebral disc (IVD), anatomical targets near the lungs or column, and areas of the brain.

BACKGROUND TO THE INVENTION

Focused ultrasound (FUS) and High Intensity Focussed Ultrasound (HIFU) have been developed for treatments of solid tumours and uterine fibroids (ter Haar, G. and Coussios, C-C. (2007). "*High Intensity Focussed Ultrasound: physical principles and devices*", Int. J. Hyperthermia 23 (2), 89-104), thrombolysis (de Saint Victor, M, Crake, C., Coussios, C.-C., & Stride, E. (2014). *Properties, characteristics and applications of microbubbles for sonothrombolysis*. Expert opinion on drug delivery (0), 1-23), drug delivery for oncological applications (Mo, S., Coussios, C.-C., Seymour, L., & Carlisle, R. (2012). *Ultrasound-enhanced drug delivery for cancer*. Expert opinion on drug delivery, 9(12), 1525-1538) and across the blood-brain barrier (Hynynen, K., McDannold, N., Vykhodtseva, N., & Jolesz, F. A. (2001). *Noninvasive MR Imaging-guided Focal Opening of the Blood-Brain Barrier in Rabbits* 1. Radiology, 220(3), 640-646) and for the treatment of neurological disorders (Elias, W. J., Huss, D., Voss, T, Loomba, J., Khaled, M., Zadicario, E., . . . Monteith, S. J. (2013). *A pilot study of focused ultrasound thalamotomy for essential tremor.* New England Journal of Medicine, 369(7), 640-648).

Chronic low back pain is one of the most prevalent musculoskeletal conditions worldwide, with 84% of adults suffering low back pain at some points in their lives. It is the leading contributor to disability and imposes huge costs to society, either directly by health-care consumption or indirectly by lost productivity. One major source of low back pain is the intervertebral disc (IVD) and there is a strong association between degenerated IVDs and low back pain. Traditionally, patients who fail in conservative treatments need invasive surgical interventions, e.g. spinal fusion and discectomy. These interventions are not ideal as they have relative high complications associated with them and the effectiveness of outcome is rather variables. A less invasive alternative for early disc degeneration which preserves motion is partial disc replacement (PDR). In PDR, the gelatinous core of the degenerated disc, called the nucleus pulposus (NP), is replaced by an implant, however current methods of removing the original degraded material leave an opening in the wall of the disc through which implanted material can be expulsed.

In many therapeutic ultrasound applications, thermally ablated lesions are formed due to a rapid temperature rise at the ultrasound focus after the sonication for periods of the order of seconds. The same principle of thermal therapy has been applied for the treatment of low back pain with an interstitial ultrasound device (Nau, W. H., C. J. Diederich, R. Shu, A. Kinsey, E. Bass, J. Lotz, S. Hu, J. Simko, W. Ferrier and J. Sutton (2007). "*Intradiscal thermal therapy using interstitial ultrasound: An in vivo investigation in ovine cervical spine.*" Spine 32(5): 503-511). Intradiscal thermal therapy aims to use ultrasound for thermal necrosis of ingrowing nociceptive nerve fibers or for coagulation and restructuring of annular collagen (Nau, Diederich et al. 2007). An MR guided HIFU system was adapted for thermally treating facet joint osteoarthritis pain in a phase I study (Weeks, E. M., M. W. Platt and W. Gedroyc (2012). "*MRI-guided focused ultrasound (MRgFUS) to treat facet joint osteoarthritis low back pain—case series of an innovative new technique.*" European radiology 22(12): 2822-2835).

Thermal based therapies may not be ideal for the removal of degenerate material which needs to be mechanically disrupted. Using short ultrasound pulses, with high amplitude but low average power, can result in intense cavitation which will mechanically disrupt tissue, by a process referred to as histotripsy (WO 2008/143998 A1) or boiling histotripsy (U.S. Pat. No. 8,876,740 B2). WO2012/131383 describes how cavitation mediated fractionation of the degenerate material can be used to reduce the tissue such that it can be removed and replaced using a fine gauge needle. This provides an ultrasound based method, which requires a very small opening in the wall of the disc, and provides a means of PDR while minimising the risk of expulsion. WO2012/131383 does not however teach how to deliver the ultrasound to the intervertebral disc.

One barrier to employing ultrasound in the IVD is that the treatment site is deeply situated in a complex anatomy with the bone structure and multiple tissue layers in the beam path. This means the ultrasound propagation is significantly distorted and so generating tightly focused beams will be challenging. A similar problem has been encountered in the transcranial and transcostal ultrasound delivery (Fink, M, G. Montaldo and M Tanter (2003). "*Time-reversal acoustics in biomedical engineering.*" Annual review of biomedical engineering 5(1): 465-497.nk, and Aubry, J.-F., M Pernot, F. Marquet, M. Tanter and M Fink (2008). "*Transcostal high-intensity-focused ultrasound: ex vivo adaptive focusing feasibility study.*" Physics in medicine and biology 53(11): 2937).

For ultrasound arrays comprising a plurality of ultrasound transducers, time reversal techniques, based on the reciprocity theorem, have been shown to be effective at creating a good focus in these environments (Fink, M (1992). "*Time reversal of ultrasonic fields. I. Basic principles.*" Ultrasonics, Ferroelectrics, and Frequency Control, IEEE Transactions on 39(5): 555-566. and Fink, Montaldo et al. 2003, and Aubry, Pernot et al. 2008). Time-reversal needs a target to focus on which can be determined a number of ways including using: hydrophone-based measurement, (Thomas, J.-L. and M. Fink (1996). "*Ultrasonic beam focusing through tissue inhomogeneities with a time reversal mirror: application to transskull therapy.*" Ultrasonics, Ferroelectrics, and Frequency Control, IEEE Transactions on 43(6): 1122-1129, and Pernot, M, J.-F. Aubry, M. Tanter, A.-L.

Boch, F. Marquet, M Kujas, D. Seilhean and M. Fink (2007). "*In vivo transcranial brain surgery with an ultrasonic time reversal mirror.*" *Journal of neurosurgery* 106(6): 1061-1066), numerical simulations based on a CT scan (Aubry, Pernot et al. 2008) and using cavitation bubble signature (Gateau, J., L. Marsac, M. Pernot, J.-F. Aubry, M. Tanter and M. Fink (2010). "*Transcranial ultrasonic therapy based on time reversal of acoustically induced cavitation bubble signature.*" *Biomedical Engineering, IEEE Transactions on* 57(1): 134-144.)

WO2012/131383 describes a method and apparatus for treatment and imaging of the IVD. It will be appreciated that imaging inaccessible sites is difficult for very similar reasons to those affecting treatment.

U.S. Pat. No. 8,545,405 describes the use of time reversal acoustics in therapeutic ultrasound treatment.

SUMMARY OF THE INVENTION

The invention provides a pressure wave system comprising a plurality of modules, each module comprising a plurality of pressure wave transducer elements, and connection means operable to connect the modules together in each of a plurality of different configurations whereby the modules can form a transmitter array having a plurality of different shapes each associated with one of the configurations.

The transmission elements on each of the modules may be arranged in a curved array. The curved arrays may be of the same shape as each other. Each of the curved arrays may have a radius of curvature which is constant along its length (or width) in at least one direction. The connection means may be arranged such that any two of the modules can be connected together, for example end-to-end, or side-to-side, in that direction, such that the two curved arrays having a common centre of curvature. For example, each of the curved arrays may be part-spherical, and the connection means may be arranged such that, in each of the configurations, the transducer elements of all of the modules together form a single part-spherical array.

Each of the modules may be of a generally rectangular shape having two sides and two ends. The connection means may be arranged such that two of the modules can be connected together side-to-side or end-to-end, or both.

Each of the transducer elements may be operable to transmit pressure waves. The system may further comprise control mean arranged to control the transducer elements on all of the modules. The control means may comprise a general purpose computer running dedicated software or a dedicated control unit. The control means may be arranged to store configuration data indicative of a current configuration of the modules. The control means may be arranged to control the transmission elements using the configuration data thereby to coordinate transmission from the transducer elements. The control means may be arranged to identify a target focal point and to coordinate the transducer elements so as to focus transmitted pressure waves at the target focal point. The control means may be arranged to vary the relative timing of transmissions from the transmission elements thereby to move the focal point of the transmitted pressure waves.

Alternatively, or in addition, each of the transducer elements may be arranged to detect pressure waves by generating an output signal in response to receipt of pressure waves. The system may comprise processing means arranged to process the output signals. Where the system comprises a control means as mentioned above, this may also serve as the processing means. The processing means may be arranged to generate an image from the output signals. The processing means may be arranged to store configuration data indicative of a current configuration of the modules, and to process the output signals based on the configuration data to generate the image.

The system may comprise a further pressure wave transducer, for example supported on a needle. The further pressure wave transducer may be arranged for insertion into a patient at a target location. The control means may be arranged to analyse the timing of ultrasound signals transmitted between each of the array of pressure wave transducers and the further ultrasound transducer. Based on the timing, the control means may be arranged to control the array of transducers to transmit ultrasound focused at the target location, or if it is an imaging system, may be arranged to process the output signals from the array of transducers, for example adjusting the imaging algorithm used to compensate for the measured transmission times between the target location and each of the transducer elements in the array.

The further pressure wave transducer may be arranged to transmit pressure waves. The control means may be arranged to analyse the times of arrival of the pressure waves at each of the array of transducers. The control means may be arranged to reverse the times of arrival to determine times of transmission from each of the array of transducers and to control the array of transmitters to transmit using the times of transmission.

Alternatively or in addition the further pressure wave transducer may be arranged to generate an output signal indicative of a received pressure wave signal. The control means may be arranged to control the transducers in the array to transmit pressure waves in sequence and to analyse the output signal to determine the relative timing of the transmission signals required to focus the transmitted pressure waves at the target location.

The needle may be a hollow needle arranged to deliver a substance to the target location or extract a substance from the target location. Indeed it may be a coaxial needle arranged to do both.

The present invention further provides a method of delivering pressure waves comprising identifying a target location, identifying an acoustic window for transmission of pressure waves to the target location, providing a modular transducer array configurable into a plurality of different configurations, identifying one of the configurations as best matching the shape of the acoustic window, configuring the transducer array in said one of the configurations, and transmitting ultrasound to the target location using the transducer array.

The step of identifying an acoustic window may comprise imaging an imaged volume including the target location. It may further comprise analysing the image, for example to locate physical features within the imaged volume. It may further comprise identifying preferred directions in which pressure waves will best propagate from or to the target location, for example using ray tracing.

Alternatively the step of identifying an acoustic window may comprise placing a pressure wave transducer at the target location, transmitting pressure waves to or from the pressure wave transducer in a plurality of directions, detecting and analysing the transmitted pressure waves to identify preferred directions in which pressure waves best propagate from or to the target location.

The present invention further provides a configurable ultrasound system comprising a plurality of transducer modules, each of which may comprise a plurality of ultrasound transducer elements, and connection means operable to connect the modules together in each of a plurality of different configurations whereby the modules can form a transducer array having a plurality of different shapes each associated with one of the configurations. The system may further comprise processing means arranged to receive data relating to a target location. The processing means may be arranged to identify, for example from the data, an acoustic window for transmission of ultrasound to the target location. The processing means may be arranged to select one of the configurations as best matching the shape of the acoustic window. The data may be image data.

The processing means may be arranged to generate, for example from the data, a 3D model of the target location. It may be arranged to determine the shape and location of the acoustic window from the 3D model.

The system may comprise a further transducer arranged to be placed at the target location. The data may be sensor output data from sensors detecting pressure waves transmitted to or from the further transducer.

The method or system of the invention may further comprise any one or more features, in any combination, of the preferred embodiments, as will now be described by way of example only with reference to the accompanying drawings.

BRIEF DESCRIPTION OF THE DRAWINGS

FIGS. 6a, 6b, 6c and 6d are a side view, perspective view, back view and front view of one module of the transducer array of FIG. 5a;

FIGS. 7a, 7b, 7c and 7d are a longitudinal cross section, back view, transverse cross section and perspective view of an alternative reconfigurable support structure which can be used with the transducer module of FIGS. 4 to 6;

FIGS. 17a and 17b show the effect of optimisation of focusing on the produced pressure.

DESCRIPTION OF THE PREFERRED EMBODIMENTS

Figure 1:
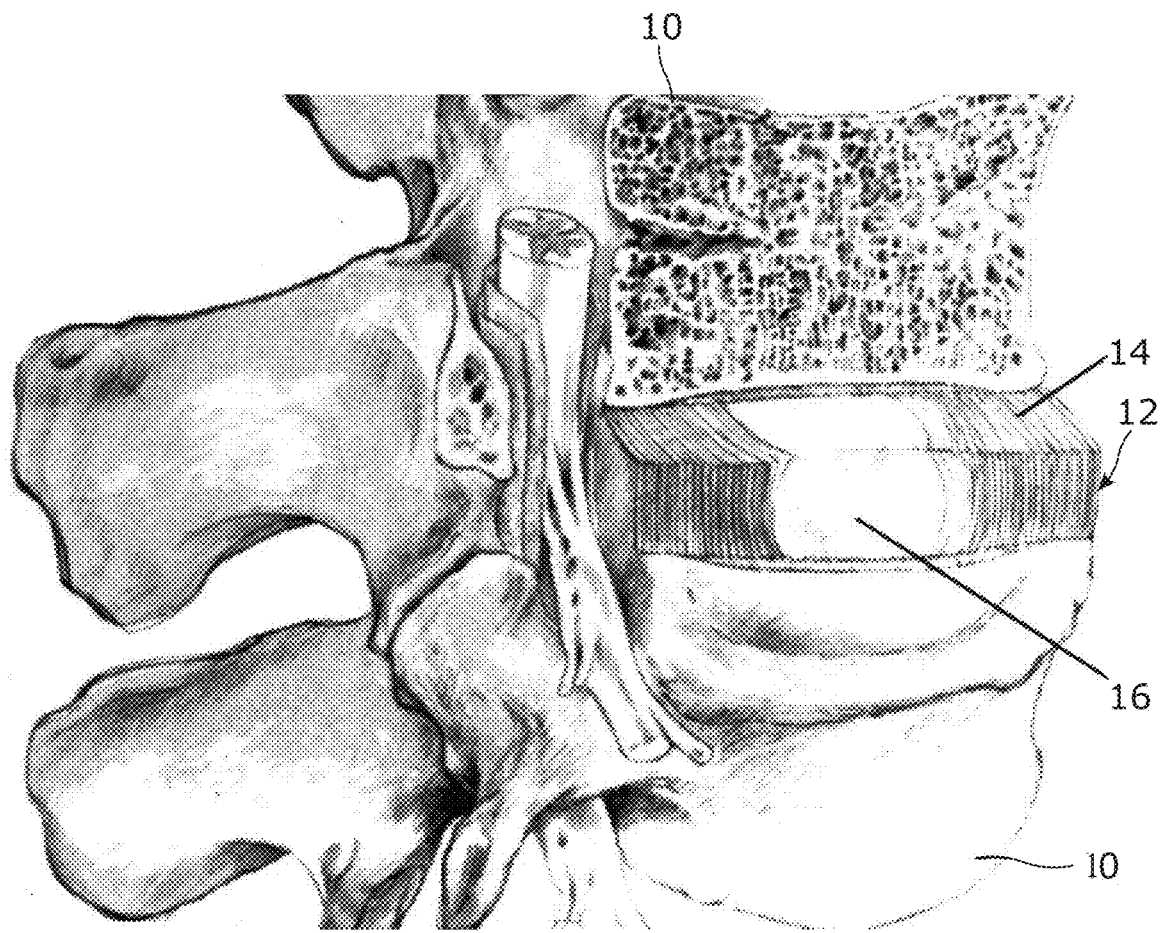
FIG. 1 is a partially cut-away diagram of a section of a human spine showing the structure of the IVD.

Referring to FIG. 1, the spine is made up of a number of vertebrae 10 and between each adjacent pair of vertebrae is an IVD 12 which provides cushioning and support to the vertebrae as the spine flexes. The IVD comprises the annulus fibrosus 14 around its periphery with the NP 16 in the centre. The annulus fibrosus is of a more fibrous tissue and provides support for, and containment of, the NP 16. The IVD further comprises cartilaginous endplates, not shown in the drawings, on the top and bottom surfaces of the IVD, which further contain the NP and provide the upper and lower surfaces of the IVD which contact the vertebrae. In some embodiments of the invention a system and method is provided for insonating the NP 16 so as to fragment the NP mechanically, without significantly affecting the surrounding annulus fibrosus 14, so that the NP material can be removed with minimal damage to the annulus fibrosus 14. In other embodiments the system may simply be used to heat or ablate parts of the intervertebral disc with the aim of achieving pain relief or denervation. In other embodiments the system may be used to achieve ablation, histotripsy or lithotripsy in the kidney, liver or pancreas through the ribcage.

Figure 2:
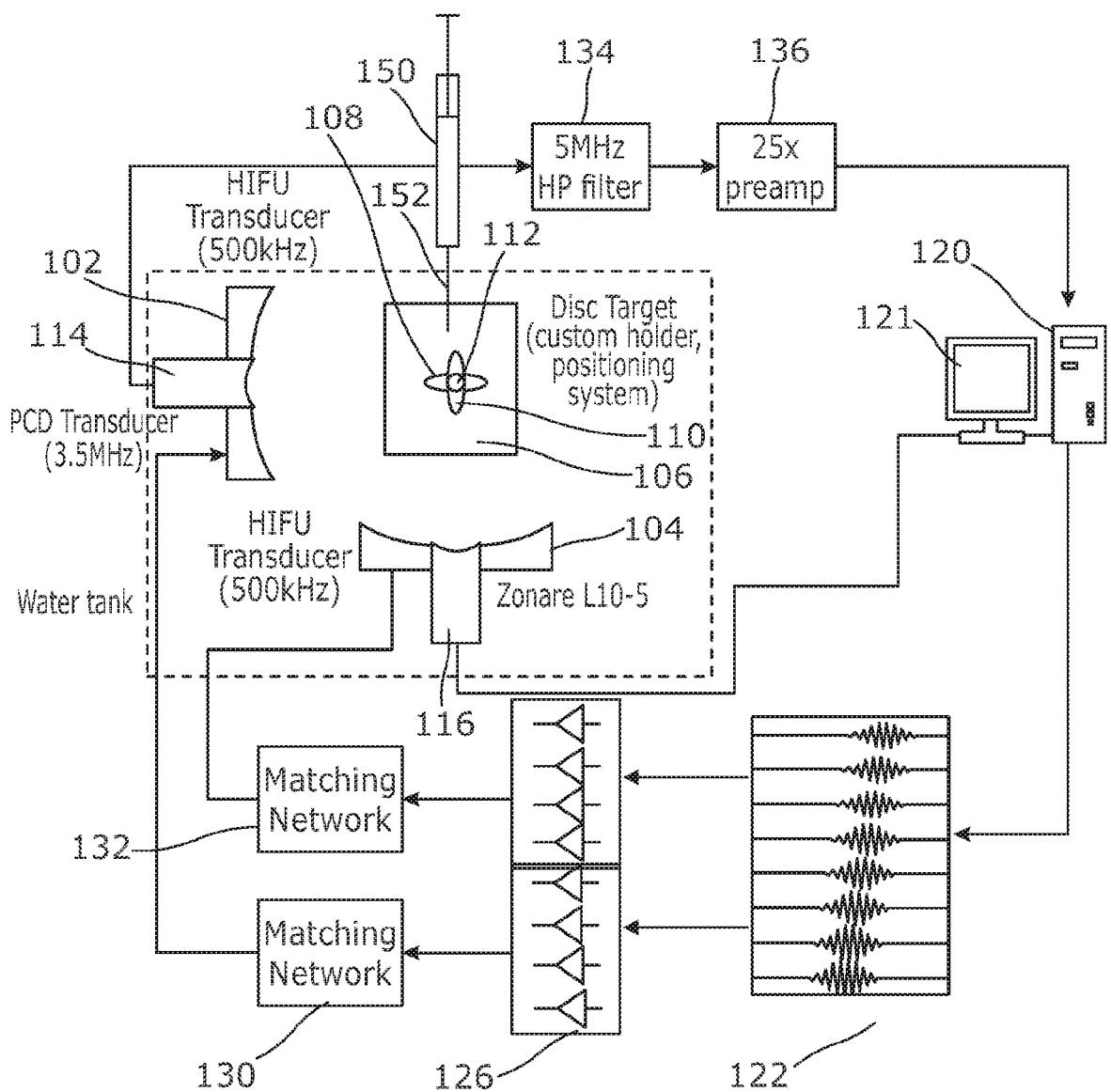
FIG. 2 is a diagram of a system according to an embodiment of the invention for removing and replacing the IVD NP.

Referring to FIG. 2, a system according to the invention may comprise at least one, for example first and second ultrasound transducer arrays 102, 104, such as therapeutic HIFU arrays, both arranged to transmit ultrasound towards a target region 106. Each of the transducer arrays 102, 104 has a respective focal region 108, 110 which is typically approximately circular in cross section but elongated along the axis of the transducer. The transducer arrays 102, 104 may be arranged so that the centres of the two focal regions coincide at a focal spot 112. Each of the transducer arrays 102, 104 may be of a modular construction, as will be described in more detail below, so that it can be configured to optimize the focusing of therapeutic ultrasound in the focal spot 112.

A passive cavitation detector (PCD) 114 may be provided, for example at the centre of one of the transducers 102 and arranged coaxially with the transducer, and may be arranged to detect ultrasound radiation generated by cavitation induced in an object in the target region 106. This may be a simple detector having a single transducer arranged to detect ultrasound at frequencies indicative of cavitation. However it may comprise a transducer array and be used for real time mapping of cavitation as described in WO2010/052494. An ultrasound imaging array 116, for example a Zonare L10-5 detector array or other similar linear or curvilinear diagnostic probe, may be provided, for example at the centre of the other transducer arrays 104, and may be arranged coaxially with the transducer array 104. The imaging device 116 may be arranged to provide B-mode ultrasound images of the disc and surrounding physiological structures and to map cavitation during HIFU exposure within the object within the target region 106. In some embodiments of the invention one or both of the PCD 114 and imaging array 116 may be omitted or located elsewhere.

A controller 120, which may be in the form of a computer having a processor and memory and arranged to run dedicated software, and may have a user interface including a user input such as a touchscreen 121, is arranged to control operation of the transducer arrays 102, 104 and to receive the output signals from the PCD 114 and imaging device 116 if they are present. A key feature of the controller is that it must be capable of addressing and controlling each element of the configurable array, and of the PCD transducer and imaging array if present, independently. The controller 120 will thus typically include multi-channel digitizers (typically at least 64, 128, 256 or 512 channels) capable of transmitting or receiving several radio-frequency (RF) lines simultaneously, such as for example one or several 256-channel Verasonics Vantage systems capable of extended transmit options and of being interconnected to an external 1000 W power supply. The skilled operator will be aware of suitable computer systems and will have the ability to program them to perform the various functions described herein, and details of the programming will therefore not be described in detail. The controller will further typically be capable of independently controlling the amplitude and phase of each signal transmitted or received to all therapeutic and diagnostic array elements within the system. In order to achieve this, the controller may incorporate or be externally connected to a multi-channel arbitrary waveform generator 122 and to a multi-channel amplifier bank 126 Each of the transducer arrays 102, 104 may typically have associated with it a matching circuit 130, 132 designed to achieve good power transmission from the amplifiers to the transducer elements. The controller 120 may be arranged to transmit trigger signals to all or to each channel of the multi-channel arbitrary waveform generator 122, which are each arranged to generate a control signal for each transducer element in the array, the form and relative timing of which determines the shape of an ultrasound pulse produced by the respective transducer array. The control signal may be input to the power amplifier bank 126, which amplifies the signal and inputs it to the individual elements of each transducer array 102, 104 via the matching circuit 130, 132. The control signals to the individual transducer elements can be coordinated so as to steer the ultrasound pulses produced by the array. This enables the focal spot 112 to be moved to place it in the desired location whilst the transducer arrays 102, 104 themselves remain stationary. The controller 120 may also be arranged to receive the output of the PCD 114, if present, e.g. via a filter 134 and a preamplifier 136 and to receive the output from the imaging device 116, if present.

The apparatus may further comprise a syringe 150 having a needle 152 which can be used to inject material into an object in the target region 106. The material may be a therapeutic substance arranged to be activated or released by ultrasound from the transducer arrays 102, 104, or it may contain cavitation nuclei arranged to lower the cavitation threshold pressure so as to encourage cavitation in the target region 106. The needle 152 may also be used to extract the material from the target region, for example the material of the IVD when it has been insonated to make it more readily extractable. The needle 152 may still further be used to inject material into the target region, for example to form a replacement NP.

Figure 3:
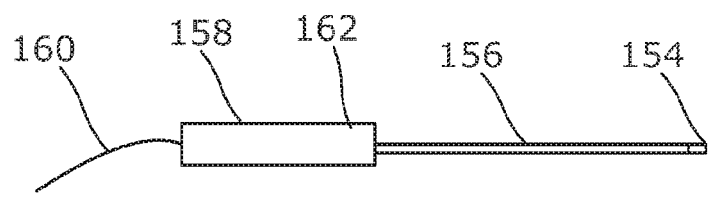
FIG. 3 is a schematic view of an implantable ultrasound transducer forming part of the system of FIG. 2.

Referring to FIG. 3, a further ultrasound transducer 154 may be provided on a separate needle 156. The transducer may be arranged to be inserted into the target region 106. The needle 156 may be connected to a handle 158 so that it can be manipulated into position by a clinician. The transducer 154 may be connected to a power supply which may be in the handle 158, or remote and connected to the transducer by a wire 160. The handle 158 may have a switch 162 operable to connect the transducer 154 to the power supply to activate it to transmit pressure waves, or it may be powered continuously. Alternatively it may be connected to, and controlled by, the controller 120. In an alternative arrangement the transducer 154 may be incorporated into the injection needle 152 so that a single needle can perform all of the functions of both needles 152, 156. The transmitter 154 may be able to generate about 1 MPa surface pressure and ideally transmits at a frequency to match that of the transducer arrays 102, 104, which may be about 500 kHz for example. The transducer may be arranged to operate as a receiver or detector in which case it may be connected to the controller 120 so that the controller 120 can receive and process detector signals that it generates in response to receiving pressure waves.

Figure 4A:
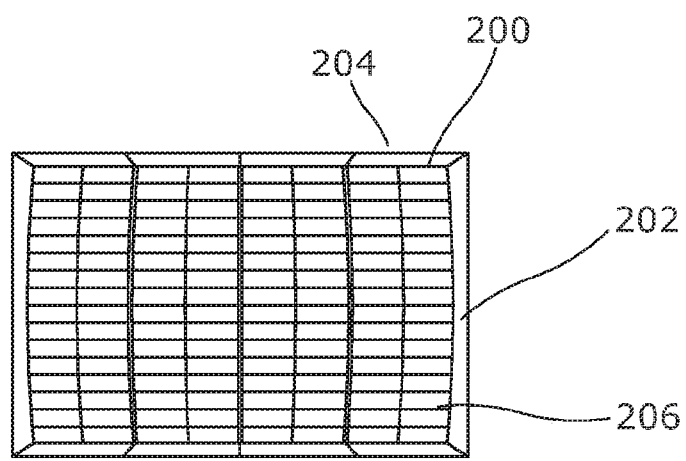
FIGS. 4a, 4b, and 4c, are front views of a modular transducer array of the system of FIG. 2 in different configurations.
Figure 4B:
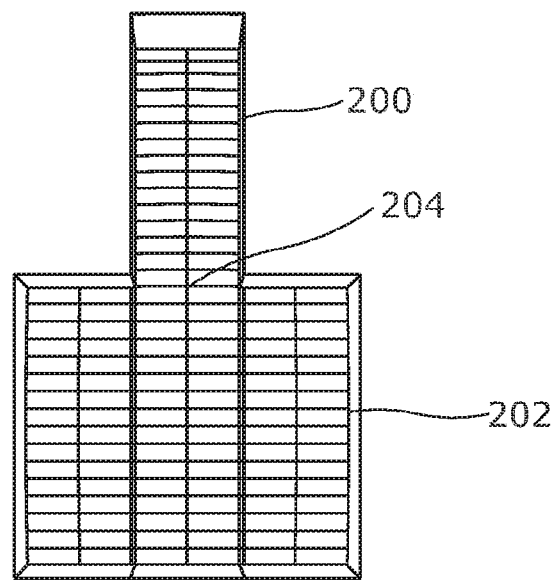
Figure 4C:
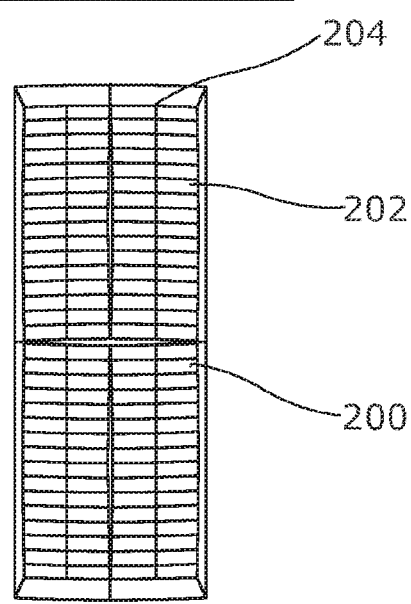

Referring to FIGS. 4a to 4c, each of the transducer arrays 102, 104 may be modular, and may comprise a number of sub-arrays or modules each formed as a separate transducer unit 200. In each case the array 102, 104 may comprise connectors or fixings so that they can be assembled together in a number of different configurations, each providing an array of a different shape. Each of the transducer units 200 may be rectangular having two longer sides 202 and two shorter sides or ends 204. The connectors or fixings may be arranged so that each of the transducer units 200 can be connected to one of the others along one side, so that they are located side by side, or along one end, so that they are located end to end. If there are four units 200 this gives rise to a number of possible configurations for example as shown in FIGS. 4a to 4c. In one configuration all of the units may be arranged in a row side by side as shown in FIG. 4a. In one of the configurations three of the units 200 may be arranged side by side, with one of the units 200 arranged end to end with one of the other three, for example the centre one as shown in FIG. 4b, or one of the end ones to form an L-shaped array. In one of the configurations the four units 200 are arranged in a two-by-two rectangular configuration. Other configurations are of course possible. The array may be made up of a different number of units.

The mounting of the transducer elements 206 on each of the units 200 may be arranged such that the transducer elements form a concave part-spherical array, i.e. all lie at respective points on a common (imaginary) spherical surface. The connections between the units 200 may be arranged such that, in all of the possible configurations, the transducer elements of all of the units 200 together form a single part-spherical array. This simplifies the control of the transducer elements in each of the units 200 and in the complete assembled array. More importantly it has the advantage that the units 200 can be completely interchangeable with each other in the complete assembled array 102, 104. However other shapes of transducer array can be used. In a modification to this arrangement, each of the units 200 may have a first constant radius of curvature in one direction and a second constant radius of curvature in another direction, with all of the units 200 being the same shape. This still provides interchangeability between the units 200.

Figure 5A:
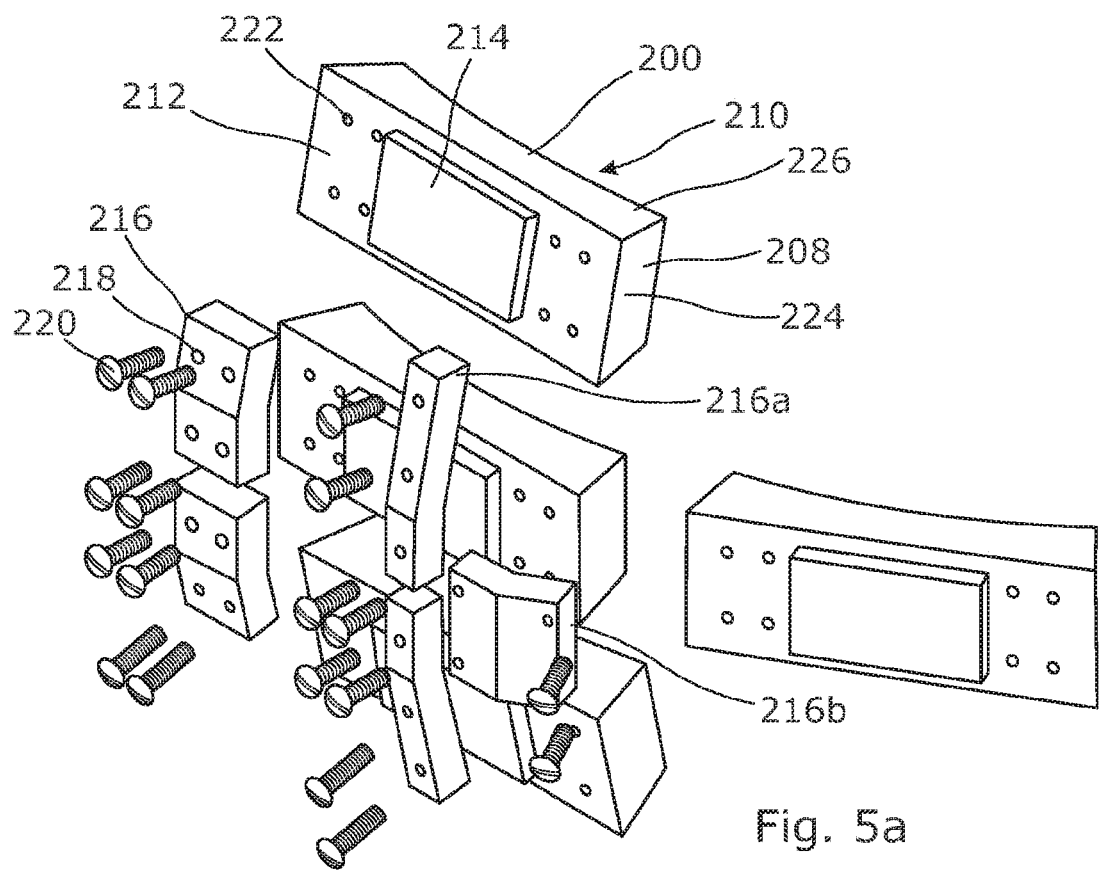
FIGS. 5a and 5b are exploded perspective views of the transducer array of FIG. 2 showing its structure.
Figure 5B:
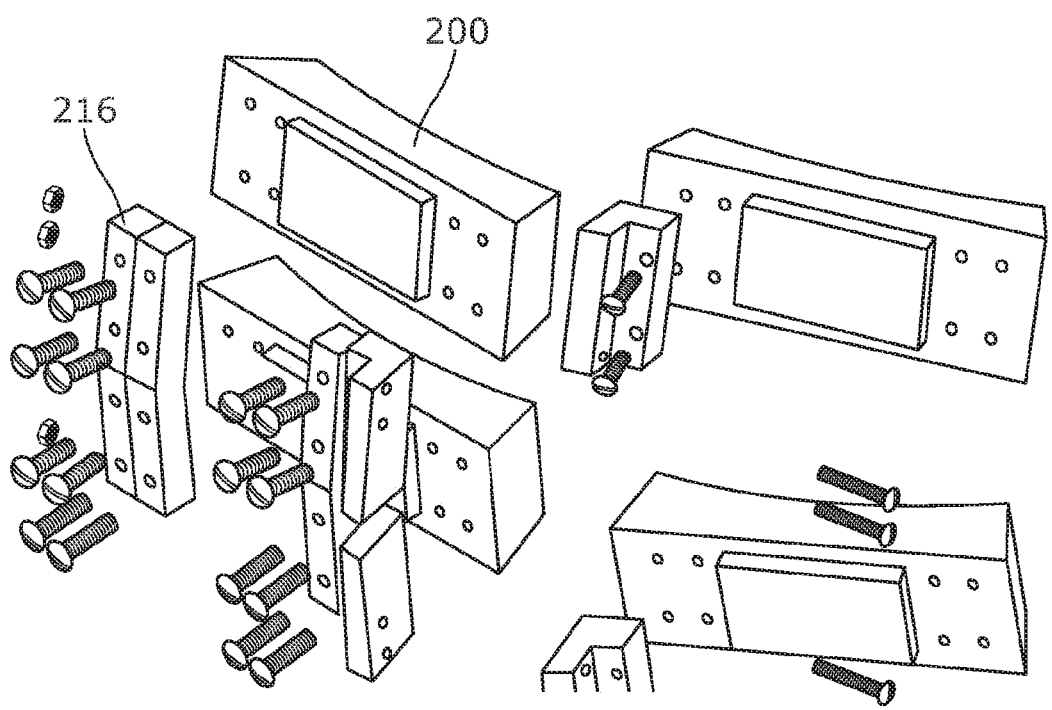
Figure 7E:
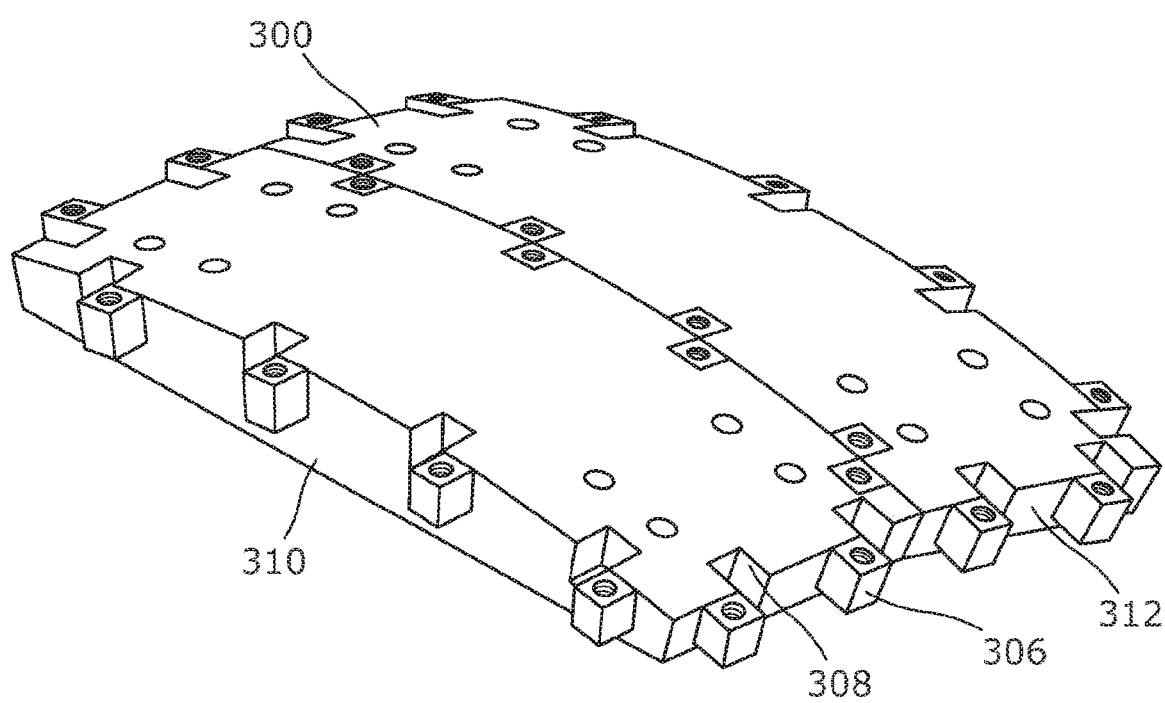
FIG. 7e is a perspective view of two sections of the support structure of FIG. 7a in an interlocked state.

As can best be seen in FIGS. 5a and 5b, each of the transducer units 200 may comprise a generally rectangular support block or housing 208 having a front face 210, which may be concavely curved in both the longitudinal and transverse directions. The radii of curvature in the longitudinal and transverse directions may be constant over the length and width of the units respectively. The radii of curvature in the longitudinal and transverse directions may be equal to each other so that the front face 210 is part-spherical. Alternatively they may be different from each other. For example the radius of curvature in either the longitudinal direction or the transverse direction may be infinite so that the transducer array is part cylindrical rather than part spherical. As the transducer elements 206 are mounted on the front face 210, the transducer array has the same curvature as the front face 210. Indeed it will be appreciated that the actual shape of the block or housing 208 itself may be varied whilst still supporting the transducer array in the various curved configurations described. The rear face 212 of the support block may be substantially flat. A connector area 214 may be provided on part of the rear face 212 to provide electrical connection to the transducer elements. The units 200 may be connected together by means of a set of brace elements 216 which may be in the form of bars or brackets, and which may have holes 218 through for receiving threaded fasteners 220 which are also arranged to engage in threaded holes 222 in the rear faces 212 of the support blocks 208. Each of the brace elements 216 is arranged to span two adjacent transducer units 200 and to be fixed to both of them, so as to rigidly connect them to each other.

The end faces 224 and side faces 226 of the support blocks 208 may be non-parallel to each other and may be radial to the part-spherical front faces 210 or transducer arrays. This ensures that, when any two of the transducer units 200, which are all of the same shape, are located against each other, the combined transducer array produced by them forms a substantially continuous concave array, which may be part-spherical, or part cylindrical, or curved in both the longitudinal and transverse directions of the units 200 with different radii of curvature. It will be appreciated that the relative positions of each pair of adjacent support blocks 208 need not be determined by the shape of the end faces 224 and side faces 226. Instead dedicated locating surfaces may be provided on the ends and sides of the units which can locate against each other to provide the required positioning. Indeed, the relative positions of the units 200 when assembled into an array may be determined purely by the brace elements 216 which hold them together, rather than by the shape of the units 200 themselves.

The brace elements 216 form a set with at least one sub-set 216a which are arranged to connect two of the transducer units 200 side by side, and at least one sub-set 216b, which may be the same subset or a different subset, arranged to connect two of the transducer units 200 end to end. This allows the transducer units 200 to be connected together in different configurations as shown in FIGS. 5a and 5b to produce different shaped transducer arrays, e.g. in the configurations shown in FIGS. 4a to 4c.

Referring to FIGS. 6a to 6d, the connector area 214 on the rear face of each of the transducer units 200 may have a set of ports 230 each of which may be arranged for connection to a cable connector 232. Each of the ports 230 may have a set of connections, one to each of the individual transducer elements 206 of the unit 200. These can provide the connection between each of the individual transducer elements 206 and the controller 120, so that the transducer elements 206 can be coordinated to create an ultrasound pulse having a movable focal spot. For example there may be three connectors 232, each providing individual connections for a third of the transducer elements 206. The cables 234 to which the cable connectors 232 are attached are sufficiently long and flexible to accommodate the various different configurations of the separate transducer units 200.

In order for the transducer arrays 102, 104 to be controlled so as to focus the ultrasound pulses in the correct position, the control system needs to take account of the relative positions of all of the transducer elements 206. Within each of the transducer units 200, the relative positions are fixed, as in a conventional array. Therefore their relative positions can therefore be defined in a suitable coordinate system, for example a polar coordinate system, and used to control them in a coordinated manner. However, for the controller 120 to take account of the reconfigurable nature of the arrays 102, 104, the configuration of the units 200, and hence the relative positions of all of the transducer elements 206 needs to be input into the controller. For example, there may be a limited number of possible configurations of the units 200 in each array, and the software running on the computer 120 may be arranged to require an input indicative of which of these configurations is being used. The input may be provided manually via the touchscreen 121, or it may be generated by an array optimization process, as will be described in more detail below. Once that information is available to the computer 120, for example defining the relative positions of the units 200 in a spherical coordinate system, that defines the relative positions of all of the transducer elements 206 in each array 102, 104, for example in a single spherical coordinate system, and so each array can be controller as required to produce a steerable ultrasound pulse. It will be appreciated that, whilst having all of the transducer elements actually located on a common spherical surface makes controlling them simple, they could be of different shapes and/or locations and still be coordinated provided those shapes and locations were known and defined.

Referring to FIGS. 7a to 7e, rather than the brace members of FIGS. 5a and 5b for fixing the transducer units together, the transducer units may be supported and held on respective mounting elements 300. Each mounting element may be of a generally rectangular shape, and may be of the same length and width as the rear of one of the transducer units 200. Each mounting element may have a front face 302 which is substantially flat and arranged to engage with the rear face of one of the transducer units 200. A securing mechanism may be provided for securing each of the transducer units 200 to one of the mounting elements, for example screw holes 304 in the mounting elements 300 which align with the threaded holes 222 in the rear of the transducer units. The mounting elements 300 may have inter-engaging fixing means that enable them to be fixed to each other in a number of different configurations. For example they may each have a series of fixing lugs 306 projecting from their side and end faces 310, 312. Adjacent to each lug 306 a recess 308 may be located, which is the same size as each of the lugs 306 so that one of the lugs 306 on one of the elements 300 can fit into one of the recesses 308 on another of the elements 300. The lugs 306 and recesses 308 may be arranged such that, for each lug 306 on one of the longitudinal sides of the mounting element 300, there is a recess 308 opposite it on the opposite side, and for, each lug 306 on one of the ends of the mounting element 300, there is a recess 308 opposite it on the opposite end. This means that all of the mounting elements 300 can be identical, and each can be fixed end to end, or side by side with any of the others. When each of the mounting elements has a transducer module 200 mounted on its front face 302, this means that the transducer modules 200 can be connected together end-to-end or side-to-side in any combination and configuration.

The angle of the side and end faces 310, 312 of each of the mounting elements, relative to the front face 302, will determine the relative orientation of each pair of adjacent mounting elements when they are assembled together. When one of the modules 200 is mounted on the front of each of the mounting elements, the angle of the side and end faces 310, 312, of each mounting element relative to the front face 210 of the module it supports, will determine the relative positions of the modules 200 in the assembled array. Therefore the side faces 310 of the mounting elements may be aligned with the radius of curvature of the transducer array in the transverse direction of the module 200, and the end faces 312 of the mounting elements may be aligned with the radius of curvature of the transducer array in the longitudinal direction of the module 200.

It will be appreciated that the mounting elements 300 do not need to be provided as separate from the transducer modules 200 and the lugs 306 and recesses 308 could be incorporated into the modules 200.

Figure 8:
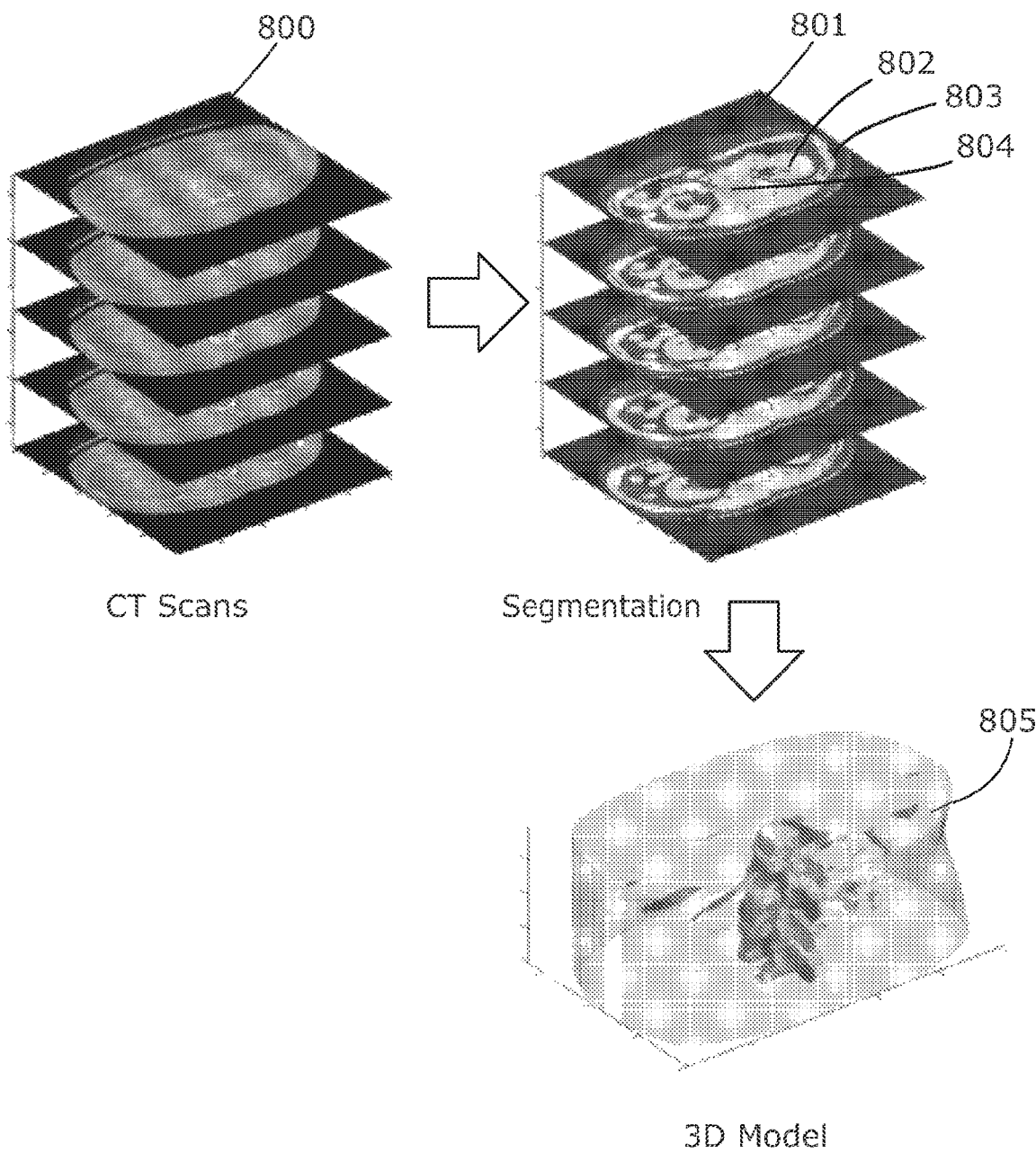
FIG. 8 is a representation of a method of generation of an acoustic 3D model of the spine of a patient from clinical CT or MRI images, forming part of a method according to an embodiment of the invention.

In use, the system may perform a variety of different functions. One function uses imaging of the patient to generate an acoustic 3D model of the region to be treated including all surrounding regions of the patient that will be between the transducer arrays and the target region when the arrays are being used. The imaging will typically be carried out using a separate imaging system, such as an X-ray CT scan or an MRI scan. Referring to FIG. 8, in order to demonstrate this function firstly image data sets were obtained for anonymous patients using KUB-CT scans 800 with a 0.625 mm slice thickness and 0.625 mm pixel size. The scans covered the anatomical structures from the vertebral body L1 to the pelvis. The dicom image data sets were imported into Matlab (R2014a, Mathworks Inc., US) and segmented into different categories of tissue or material, in this case air 801, soft-tissue 802, fat 803 and bone 804, using thresholds on the Hounsfield units. The cancellous bone on the vertebral bodies was classified as soft-tissue using the threshold method, however because it was surrounded by a cortical shell which segmented as bone, the Matlab imfill command was used to convert the pixels to bone. In some cases the cortical bone was too thin to completely enclose the cancellous body and in these cases the regions were manually corrected. The segmentation of soft-tissue into fat and other soft-tissue was deemed an acceptable approximation from the point of view of acoustic propagation as most soft-tissue has similar acoustic properties with the exception of fat. It will of course be appreciated that the tissue could be categorized in different ways depending on the site of the target region and the processing power available. After segmentation, the processed CT images were stacked to form a 3D model 805 that was loaded into the acoustic simulation software package.

Figure 9C:
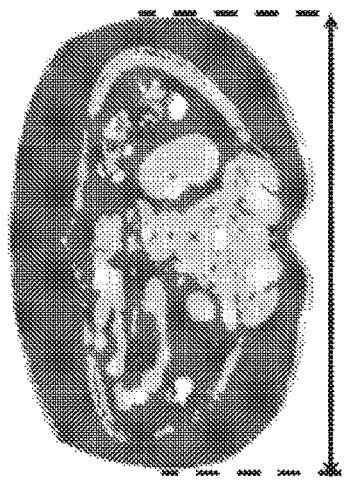
FIGS. 9a, 9b and 9c are horizontal planar images of acoustic models of patients of different BMI.
Figure 9B:
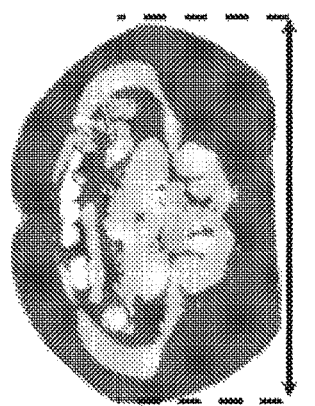
Figure 9A:
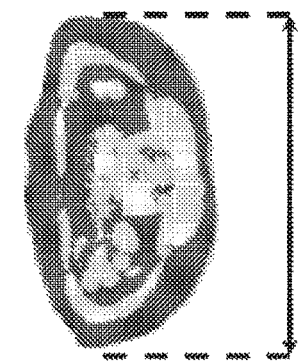

Referring to FIGS. 9a, 9b and 9c, in order to investigate the effect of the size of patients, CT scans from three patients were segmented to produce the acoustic maps shown. They will be referred to as model I (small), model II (medium), and model III (large), and had circumference of 789 mm, 929 mm and 1129 mm respectively and lateral widths of 290 mm, 320 mm and 380 mm. Because there is the possibility of degeneration for every lumbar disc, the four discs from vertebral body L1 to L5 were all modelled by the simulation tool. It was not possible to automatically segment the IVD from the CT images as the Hounsfield units of the IVD were very similar to the surrounding soft tissue. Instead it was assumed that the soft tissue between two consecutive vertebrae was the IVD; the outline of the vertebrae was superimposed on the soft tissue from which the IVD boundary in the soft-tissue was segmented.

Figure 10:
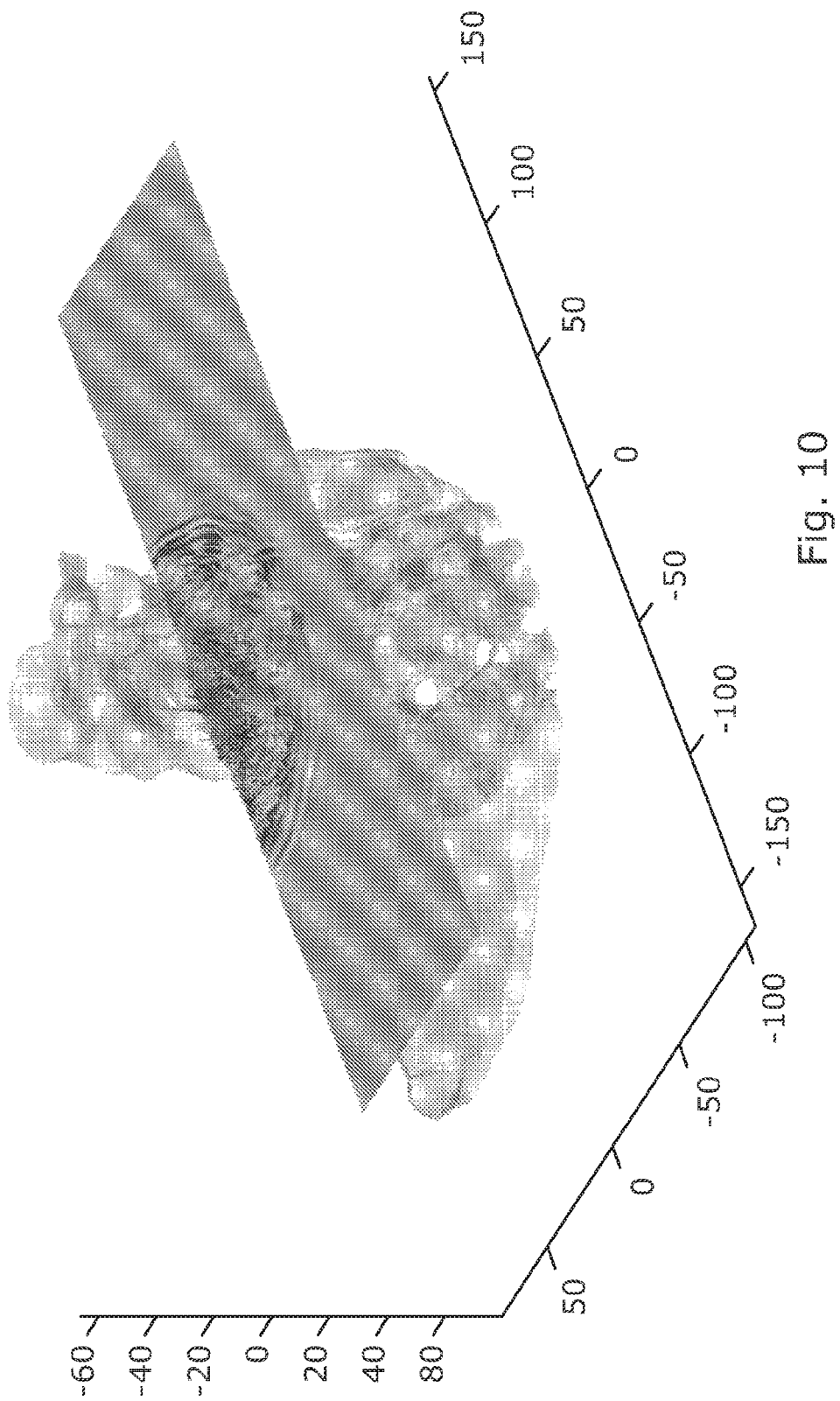
FIG. 10 shows a 3D model and part of that model used in a 3D simulation.

PZFlex (Weidlinger Associates, Ltd) was used to simulate the ultrasound propagation. PZFlex employs the finite element method and an explicit time-domain algorithm to solve locally linearised version of the continuity, momentum and state equations directly (rather than combining them into a wave equation). Hexahedral element with 8 nodes was used for regularly meshing the model. The grid spacing of 15 elements per wavelength was chosen for the compromise between a nice accuracy and computational burden. Although the size of computation domain of simulations was varied for different patients and IVDs, the whole targeted IVD and the adhered vertebral bodies were all included in the models the average size of which was 100*370*175 $mm^3$. Referring to FIG. 10, due to the limited PC memory, only the posterior part of patient, in the regions above and below the plane shown, was included in the model. Since the intestinal cavities filled with air in the anterior part would prohibit the propagation of ultrasound, this simplification would not affect the results. All the simulation results were post-processed and visualised in Matlab.

Figure 11:
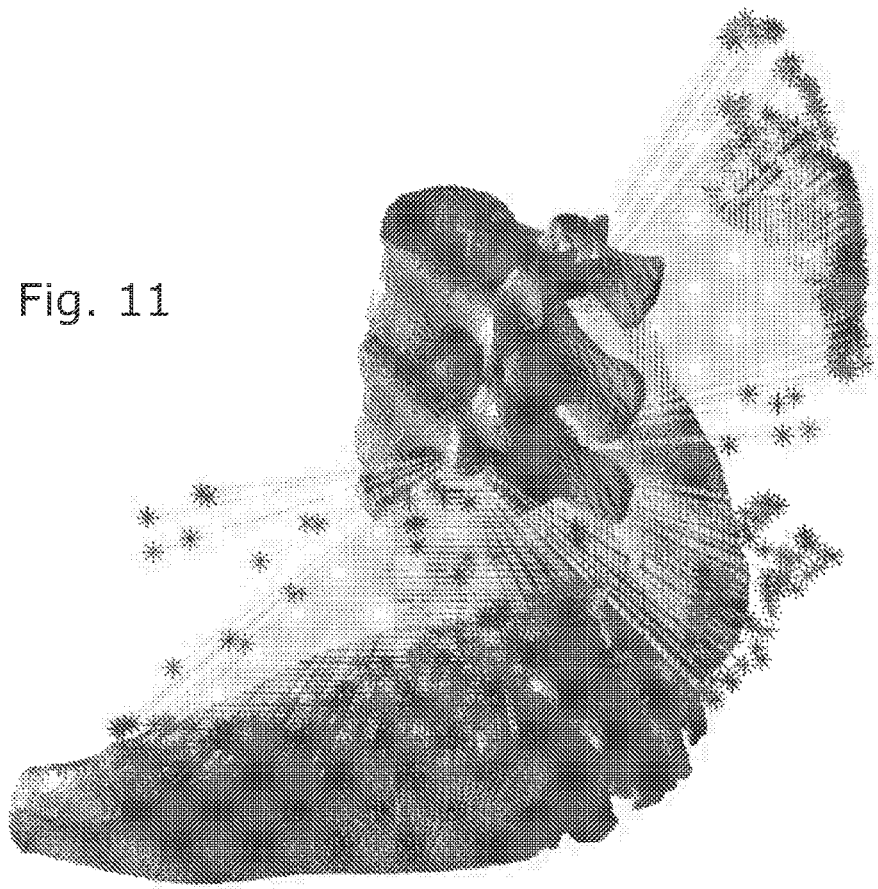
FIG. 11 is a representation of ray traces used in a reciprocity simulation forming part of a transducer optimization process according to an embodiment of the invention.
Figure 12:
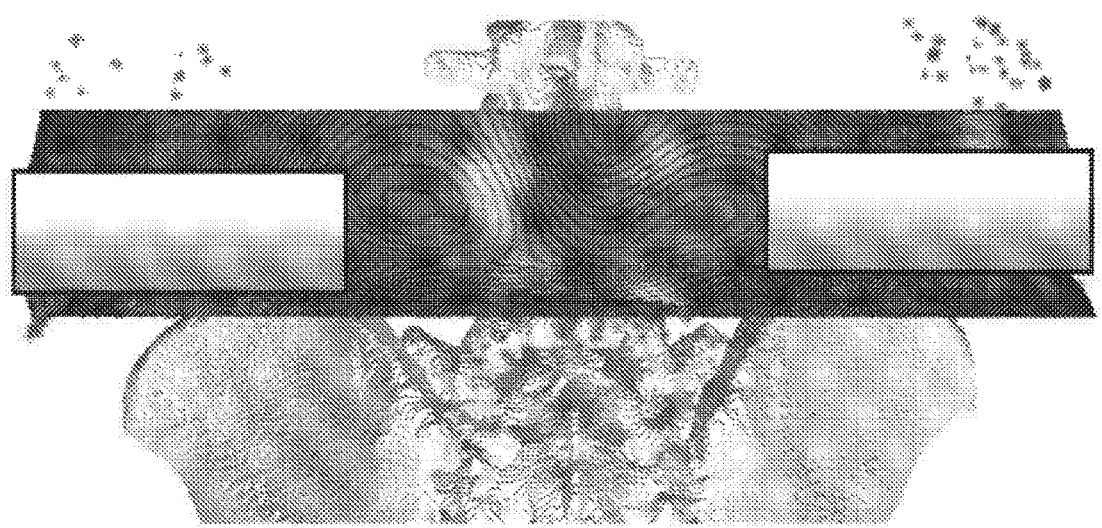
FIG. 12 shows selected acoustic windows obtained from the reciprocity simulation of FIG. 11.
Figure 13:
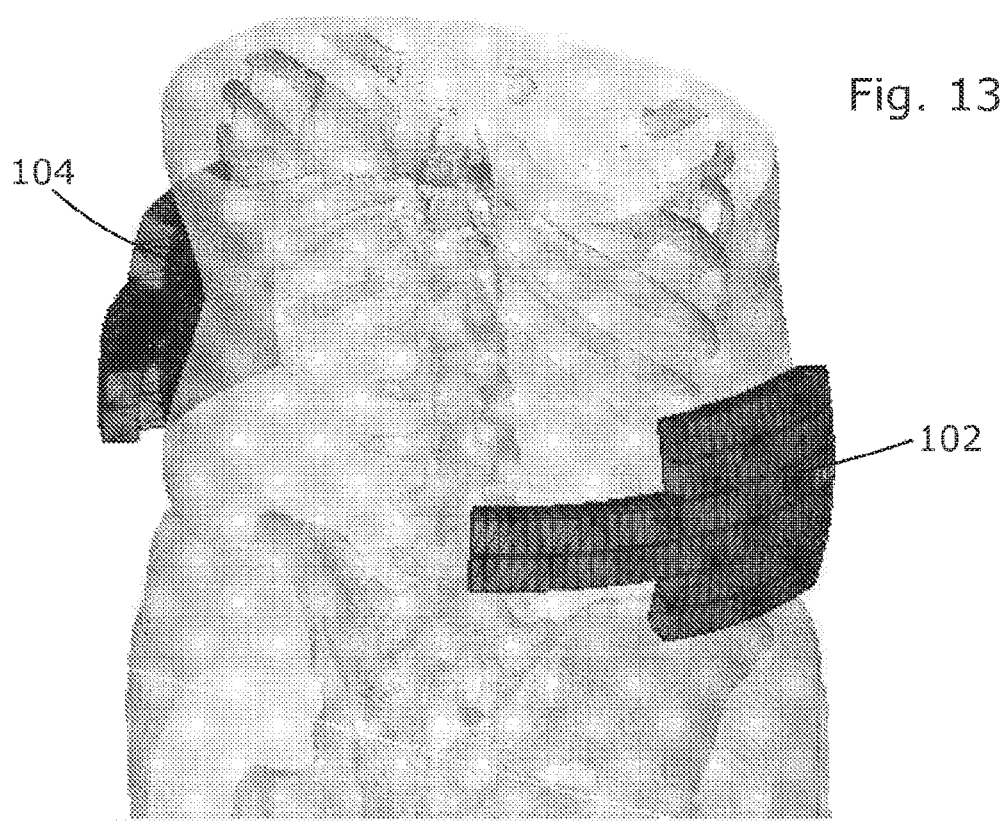
FIG. 13 shows positioning of the configurable transducer array for treatment or imaging of the spine.
Figure 14:
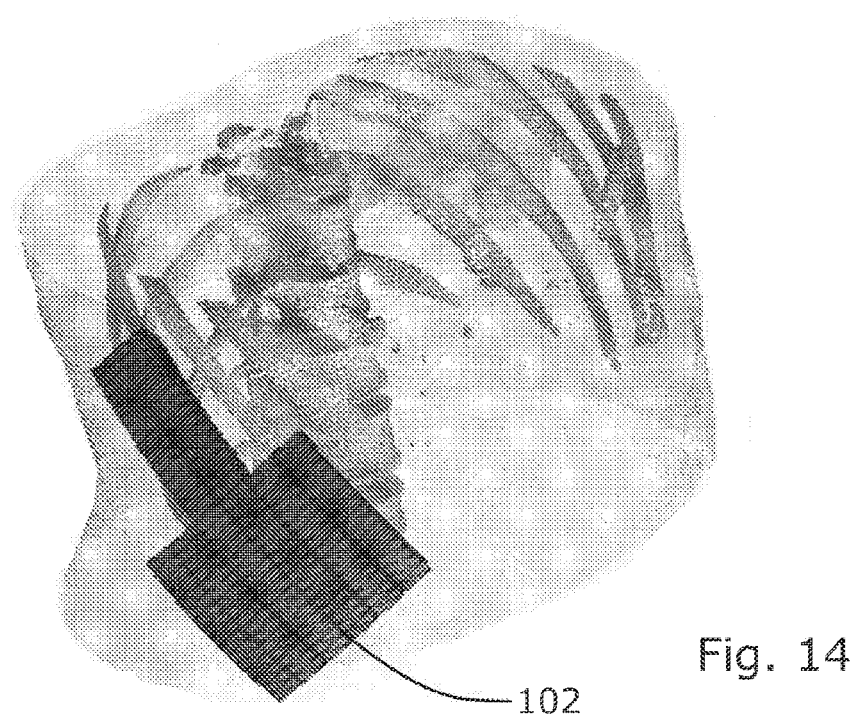
FIG. 14 shows an alternative positioning of the configurable transducer array of FIG. 13 for treatment or imaging of the liver through the ribcage.
Figure 15:
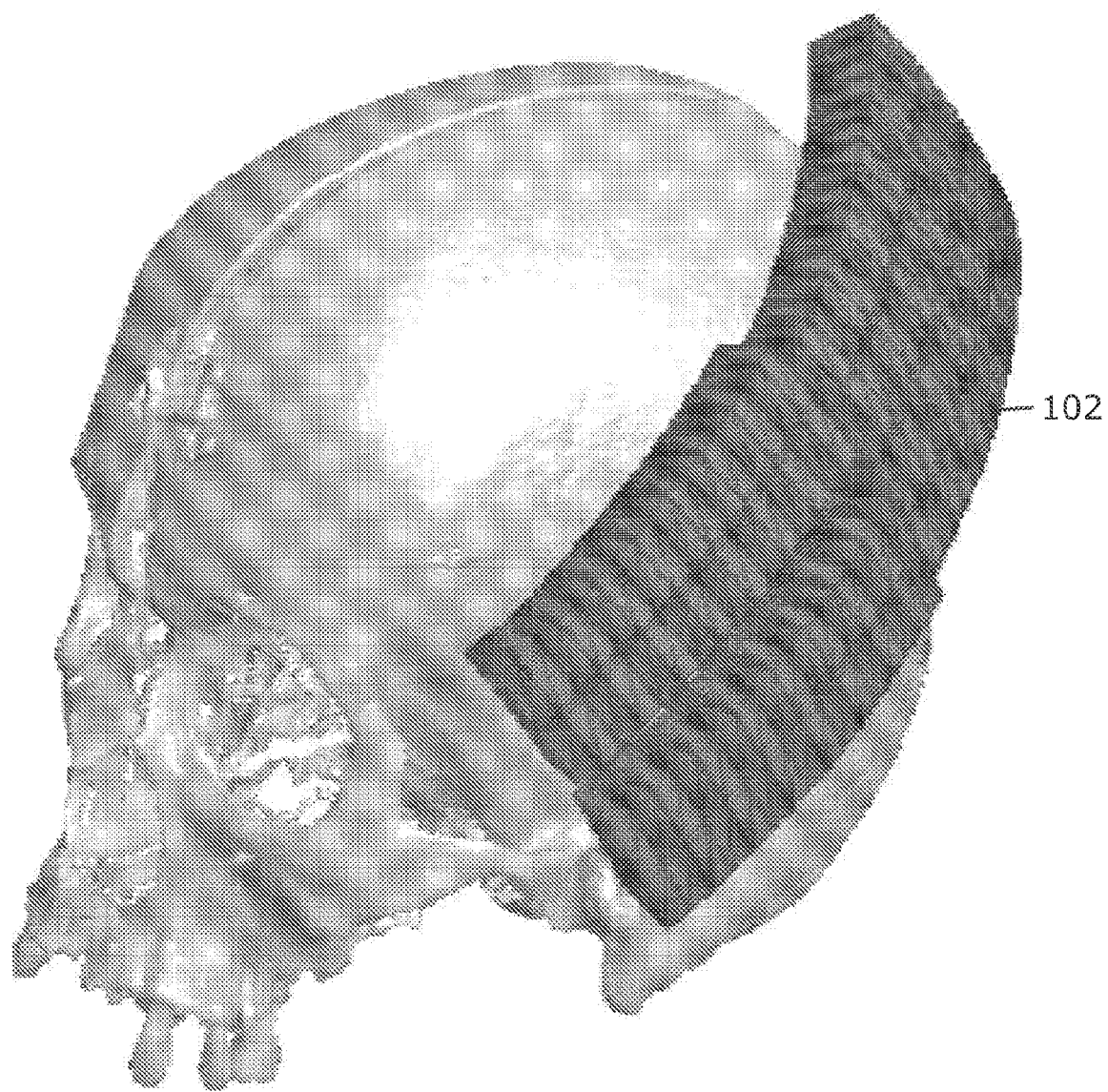
FIG. 15 shows a possible positioning of the configurable transducer array of FIG. 13 for imaging or treatment the brain of a patient through the skull.
Figure 16A:
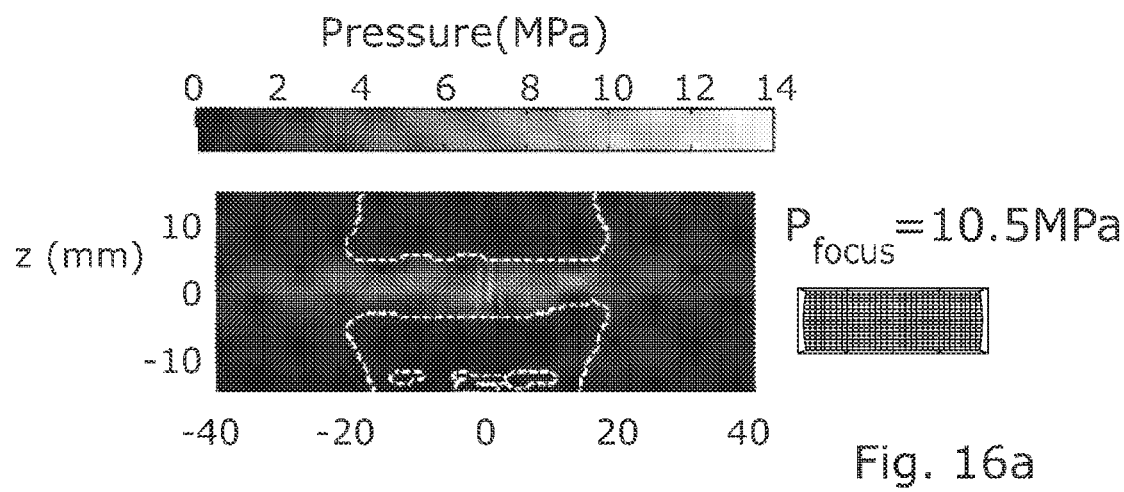
FIGS. 16a to 16h show maps of acoustic pressure generated in the region of an IVD of two different patients using different transducer array configurations.
Figure 16B:
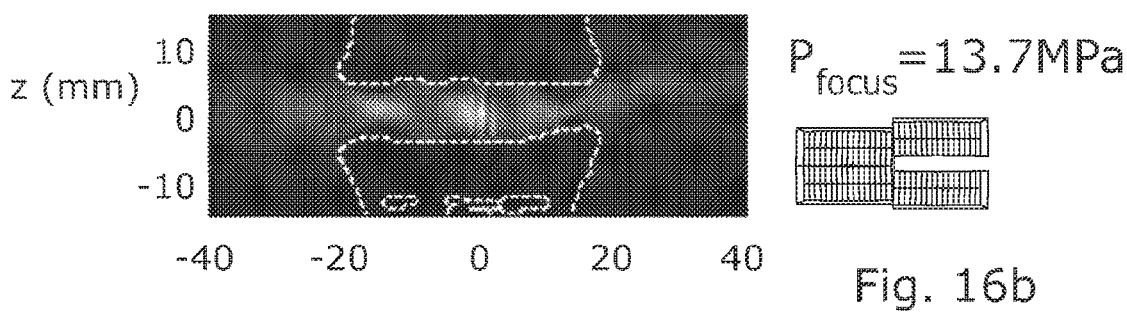
Figure 16C:
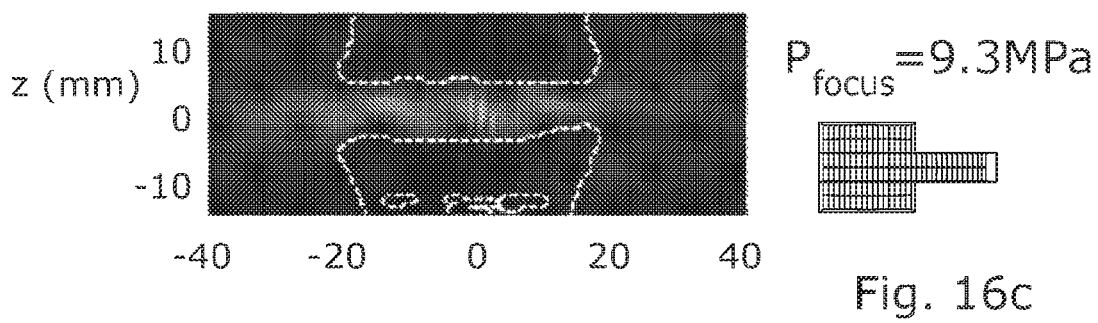
Figure 16D:
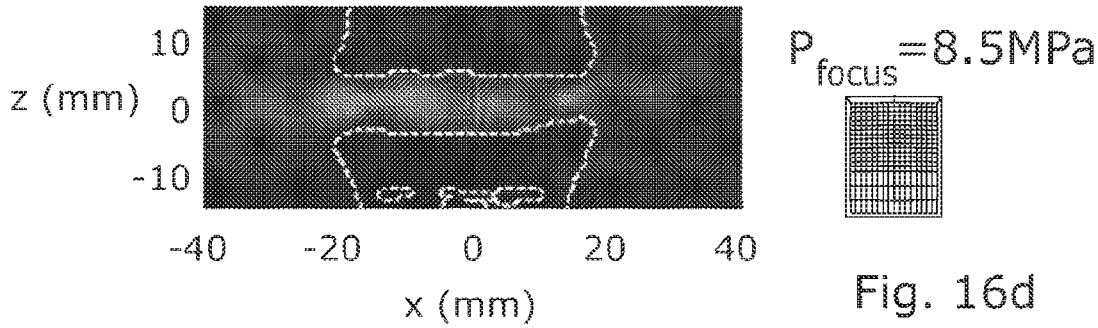
Figure 16E:
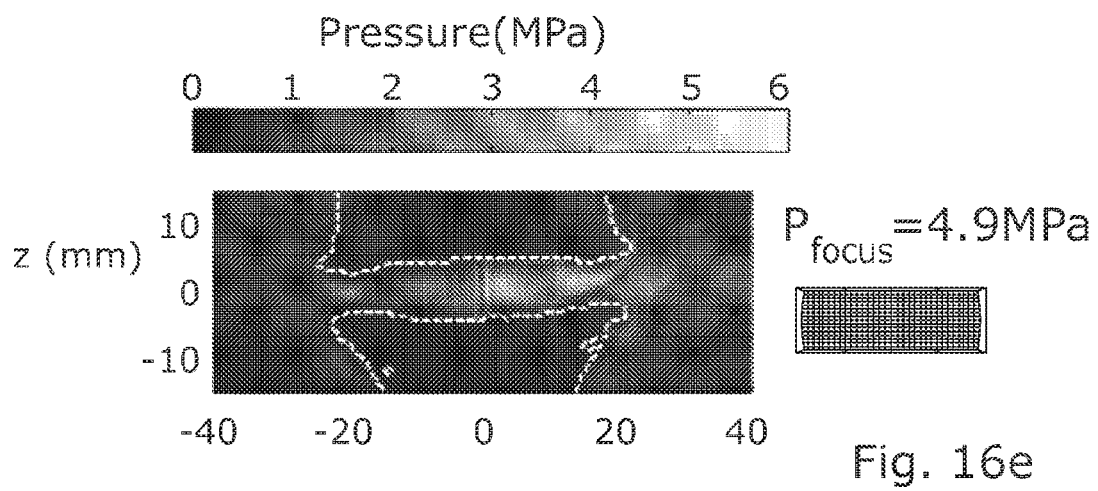
Figure 16F:
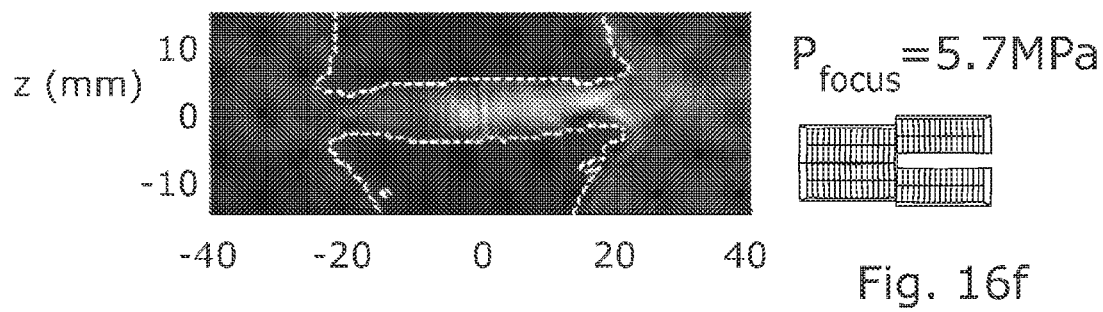
Figure 16G:
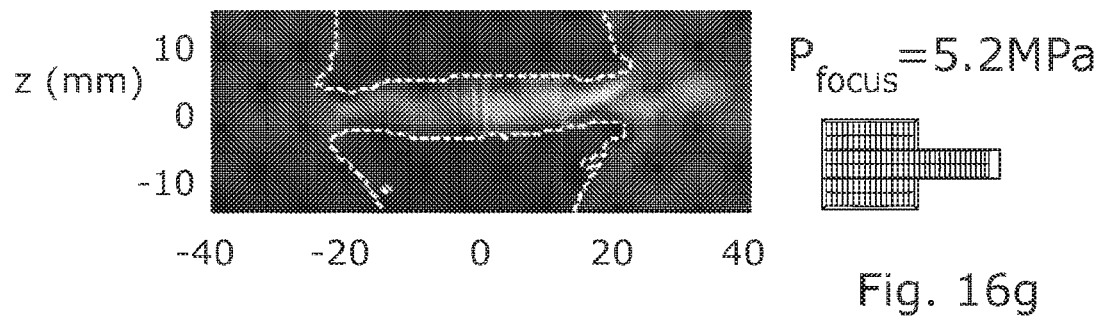
Figure 16H:
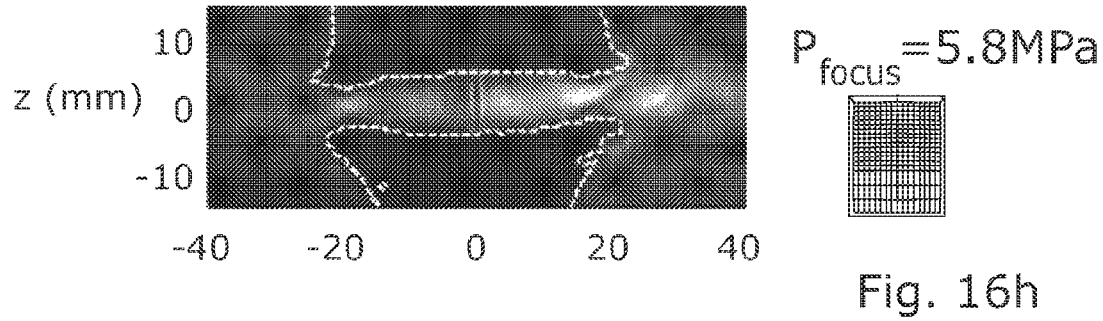

Referring to FIG. 11, in order to determine the optimum transducer array locations, in the simulation model, a point source generating a pure 500 kHz sinusoidal waveform was located at the centre of the IVD, and the pressure waveforms over a simulation period of time at all points on a spherically curved surface outside the patient body were calculated and recorded. To do this, properties including density and elasticity were allocated to each of the categories of tissue or material, and location rays were simulated as being cast out from the same point source to the surface of the skin as straight lines without considering refraction for simplicity. Rays that reached the skin surface are shown in FIG. 11. The complete waveform including the phase and amplitude of each of these rays was calculated over the whole of the simulation period. From this simulation, preferred directions in which pressure waves will best be transmitted to or from the target location could be identified. The locations and shapes of the acoustic windows, i.e. the areas of the curved surface over which the maximum acoustic power from the point source is received, was calculated. Two appropriate acoustic windows, one on either flank of the patient, were identified, in this case by overlapping the outputs of the ultrasound propagation and ray tracing models as shown in FIG. 12. Given an assumed size and shape of the transducer arrays that can be located anywhere on the curved surface, the optimum positions of the transducer arrays to best cover the acoustic windows was calculated. The optimum locations of the transducer arrays, assuming a rectangular configuration of the transducer arrays, are indicated in FIG. 12. These correspond to optimized locations of the two transducer arrays shown in FIG. 13. A similar process could be followed to identify optimal acoustic windows and array configurations for sound transmission through the ribcage, illustrated in FIG. 14, or the skull, shown in FIG. 15.

In the simulation, over each acoustic window an ultrasound array was generated that consisted of 192 rectangular elements each of dimensions 5 mm×3 mm tightly arranged in 3 rows of 64. The transmit signals for each element was obtained by time reversing the recorded waveforms at the location of the element from the simulation with a point source.

The effect of different configurations of transducer array were investigated in the simulation by defining different shaped transducer arrays and optimizing the position of each of them to cover the acoustic windows. The transmit signals for each of the transducer elements in each case were then calculated, again by reversing the recorded 'received' waveforms with a point source, and the resultant acoustic signal at the location of the IVD was calculated. The results of this simulation are shown in FIGS. 16*a* to 16*d* for a low BMI patient, and in FIGS. 16*e* to 16*h* for a high BMI patient. For a fixed input power into the configurable array, the largest pressure at the focus is achieved in the low BMI patient for the configuration shown in FIG. 16*b*, whilst for the high BMI patient this is achieved for the alternative configuration of FIG. 16*c*.

In use, the patient may be scanned prior to the procedure to generate a series of images which may be uploaded onto the computer system 120, and the computer system 120 may be arranged to generate a 3D image of the patient and then to calculate the optimum configuration and position of the transducer arrays as described above. For this calculation, while the amplitude of each of the simulated rays at the point where it reaches the spherically curved surface is used, the phase information is not needed. For any modular transducer array there will only be a limited number of configurations, which may be stored in memory in the computer system, and the system may be arranged to search over all possible positions of each of the configurations to identify the optimum combination. The arrays 102, 104 may then be assembled into the optimum configuration, placed in the optimum position relative to the patient and connected up to the computer system 120 using the connectors 232. The configuration of the arrays 102, 104 may be input to the computer system by the operator. Alternatively there may be only one operable combination of transducer modules for each array configuration, in which case the computer system can assume the relative positions of each part of the transducer array when controlling the transducer.

In an alternative method of optimizing the shape and location of the transducer arrays 102, 104, the transmitter 154 may be inserted into the target location and controlled to transmit an ultrasound signal. The configurable array itself, or a larger array with lower resolution, may then be used, either in a stationary position, or being moved continuously around the patient, or moved between a number of selected positions and configurations, to detect the ultrasound over an area around the patient in the region where the optimum acoustic window is expected to be located. From the output signals from the detector array the optimum position and configuration of the array can be determined.

Once the optimum configuration of the arrays 102, 104, and their optimum location relative to the patient, have been determined, and the transducer arrays 102, 104 have been set up, the array needs to be focused onto the target area. To do this, a time reversal calculation may be carried out using the transducer arrays 102 104 configured into the optimum configuration and located at the optimum location relative to the patient, and the ultrasound source 154. The source 154 may be inserted into the patient, for example into their spine until it is at the target location e.g. in the NP. This can be achieved for example using surgical guidance such as fluoroscopic or endoscopic imaging. The source 154 may then be activated, and the acoustic signals received at each of the transducer elements 206 of each of the transducer arrays 102, 104 over a test period recorded by recording the output signals from each of the transducer elements over that period. The time between the transmission of an ultrasound signal from the source 154 and the arrival of the transmitted signal at each of the transducer elements 206 in the arrays 102, 104 indicates the transmission time between each of the transducer elements 206 and the source 154. As the transmission times will, in general, all be different, the received ultrasound signals at each of the transducer elements, and hence the output signals generated by each of the transducer elements, will be out of phase with each other with phase offsets between them which are dependent on the different transmission times. The recorded transducer output signals may then be reversed to generate control signals for each of the transducer elements 206 which will generate ultrasound signals, from the transducer elements 206, having phase offsets which are the reverse of those of the received ultrasound, which will arrive in phase with each other at the location of the source 154, and hence optimally focus transmitted ultrasound at the point where the source 154 was located. The transducer arrays 102, 104 may be activated using the calculated control signals to focus ultrasound at the target location. This can be done very rapidly while the transmitter 154 is still in place. Therefore, if the transmitter is incorporated into the syringe needle 152 of the system of FIG. 2, the optimized focusing can be used as part of the treatment or replacement of the NP.

Once the relative phase offsets of the optimally focusing control signals to control the transducer elements 206 to generate ultrasound focused at the initial target location have been determined, the focal point of the ultrasound can be moved by modifying relative timings of the control signals to the different transducer elements to modify those phase offsets. For the controller 120 to do that, it may have stored in memory the transmission times between each of the transducer elements and the target location, as well as the relative positions of all of the transducer elements 206 on each of the modules 200. From that information it may be arranged to recalculate the transmission times for a different target location close to the initial target location. These transmission times may be calculated using just the changes in distance between the transducer elements and the new target location, on the basis that the tissue type and therefore transmission speed will not vary significantly between the different locations. However the calculations may also take into account the type of tissue between each of the transducer elements and the new target location, as determined form the 3D model. From these transmission times it can then generate the transmission signals as required to focus ultrasound at the different target location. This allows the focus to be moved around, for example to fragment different parts of the NP. Regardless of the level of detail for calculating the new transmission times for each new target position, the transmitter 154 may be moved to one or more further positions and transmit further signals, and the arrival times of those signals at the transducer elements 206 used to generate new transmission times for the new position. The more positions of the transmitter 154 are actually used, the less accurate the calculations for interpolating between those positions needs to be.

In an alternative arrangement, the transmitter 154 on the needle may be replaced by a receiver, arranged to generate output signals in response to the receipt of ultrasound signals. The receiver may be connected to the controller so that it can receive and record the output signals from the receiver. The controller may then be arranged to activate each of the array of transducers 206 in turn and time and record the output signal from the needle-mounted receiver in response. Once this has been done for each of the array of transducers, the transmission time between each of them and the receiver can be calculated, and used to calculate the required timing for a control signal to each of them that will result in the ultrasound from all of them arriving in phase at the location of the needle-mounted receiver, i.e. to focus the transmitted ultrasound at that point.

An example of a complete procedure for the replacement of the damaged NP will now be described, as an example of the application of the present invention. First the syringe 150 is filled with material containing cavitation nuclei. These may be in the form of nanoparticles fabricated from polymer material, such as polydiallyl dimethyl ammonium chloride (PDADMAC), having particles of, for example, silicon dioxide attached to their surfaces to roughen the surface, or they may be in the form of polymeric nano-cups. However other types of sonosensitive particles or gas-filled ultrasound contrast agents or other contrast agents can be used. The needle 152 of the syringe may be inserted into the NP 16, and the cavitation nuclei injected into the NP 16 through the needle 152 of the syringe 150. This injection step can be carried out under surgical guidance (typically done under fluoroscopic or endoscopic imaging, but not necessarily). The injection step may also be done using minimally invasive techniques, but not necessarily. The injection may be controlled as far as possible so that the cavitation nuclei are confined to the NP and do not spread to the annulus of the IVD.

The needle 152 may then be left in place and the transmitter 154 activated to calculate the optimum transmission signals for each of the transducer elements 206, and during insonation using those optimized signals. The needle 152 may then be used for subsequently extracting the fragmented NP tissue.

During the insonation the therapeutic transducers 102, 104 are then positioned and controlled so that their pressure foci 108, 110 coincide at a point 112 inside the NP 16 of the disc to be treated. During the treatment the focus may be moved by varying the relative timing of the transmission signals to the individual transducer elements 206, so that it is located at different points in the NP. The resulting cavitation and fragmentation of the NP may be imaged in real time during the treatment using the ultrasound imaging array 116 contained within the therapeutic transducer device 104, but can be achieved using other means of guiding and alignment such as fluoroscopic imaging and/or computer-based patient registration techniques that might not necessarily form part of the therapeutic device, but that can be associated with it.

This treatment regime is distinct from thermal ablation—it typically uses higher pressure amplitudes delivered in short pulses, with a much lower duty cycle than thermal treatment. The goal of this treatment is explicitly to minimise any thermal effects on the surrounding tissue. The insonation is pulsed with short pulses of three to fifty cycles, low duty ratio of 0.1 to 5% and high pressures of up to 20 MPa peak rarefactional focal pressure (PRFP) or 80 MPa peak positive focal pressure (PPFP). The PRFR may in some cases be anywhere within the range 5-80 MPa, but will generally be less than 50 MPa.

During the insonation, as the NP tissue is being fragmented, the NP is monitored to monitor the location, progress and extent of treatment, and in particular of the fragmentation, using the acoustic sensors contained within the device. In this embodiment these include the single element passive cavitation detector 114 and the multiple element passive cavitation detector 116. However, they can include a B-mode imaging transducer, and a passive imaging detector array, for example as described in WO2010/052494.

Once a sufficient amount of the tissue of the NP has been fragmented, the fragmented tissue is extracted. This extraction of the mechanically fragmented tissue can be performed using either the needle 152 that was used initially for the insertion of artificial nuclei, or another needle inserted specifically for the purpose.

In some cases only one insonation and one extraction step may be sufficient. However in other cases, after a first extraction step, further insonation and extraction steps may be performed. In some cases, where repeat insonation steps are performed, further cavitation nuclei are injected for each insonation, though in some cases this may not be necessary.

B-mode or other imaging techniques can be used to check that fragmentation and extraction is complete. Once a sufficient amount of the damaged NP has been extracted, a suitable biocompatible polymer is inserted into the space that has been created within the NP 16. This polymer can be one of a number of suitable polymers, for example protein hydrogels or curable polyurethanes, the defining characteristic of these being that they can be injected in liquid form and undergo in situ hybridization once in place to form a hydrogel that mimics the properties of the healthy NP.

As mentioned above, passive acoustic mapping, for example as described in WO2010/052494 may be used to monitor acoustically induced cavitation during therapy. Where the region being imaged (and treated) is inaccessible, such as in the spine, the problems described above in getting ultrasound to the target region apply equally to receiving sufficient ultrasound from the imaged region to generate a useful image. Therefore the modular transducer array described above may also, or alternatively, be used for imaging. While this may be useful in various imaging methods, passive acoustic mapping is a good example as it requires the detection of ultrasound, or more generally pressure waves, generated by cavitation events, which may themselves be occurring in an inaccessible location. For example, referring to FIG. 2, the passive cavitation detector 114 may be incorporated into the modular transducer array, as one or more of the modules 200, or indeed as part of one of the modules 200. Since attenuation of the ultrasound or other pressure waves is frequency dependent, and the PCD 114 typically detects at frequencies significantly higher than those at which the HIFU transducer operates, the modelling as described above with reference to FIG. 11 may be performed for each of the two different frequencies or frequency ranges. The data produced may then be used by the controller 120 to determine the optimum configuration and location of all of the modules. For example optimum configuration and location may be selected so as to maximize the 'received power' at the array, taking into account the different detection frequencies of the different parts of the array. Alternatively either the PCD part of the transducer array, or the HIFU part of the array, may be given higher weighting in the optimization process.

As with the transmission-only arrangement, once the modular combined PDC/HIFU array is located in the optimum location relative to the subject, the transmitter 154 may be used to generate an ultrasound signal at a target point to be imaged, and the arrival time of that signal at each of the transducer elements of the PCD 114 used to determine the transmission times between the target point and each of the transducer elements. Once these times have been determined, they can be used to modify the imaging algorithm, which typically uses time shifting of the signals at each transducer in the imaging array to identify the signal generated at each point in an imaged area or volume. For example in the passive acoustic mapping method of WO2010/052494 the propagation distance between each of the array elements and the target location may be adjusted to account for the different speeds of propagation. Once this adjustment has been made for one target location or imaged point, the same adjustment can be used for all imaged points provided the imaged area is small which is typically the case.

While the invention has primarily been developed for the treatment of the NP or other parts of the spine, delivering ultrasound to some parts of the brain or other parts of the skull can be similarly challenging, and the system of FIG. 2 can be used for treatment of the brain. One of the transducer arrays 102 may be used in an optimized configuration and location for transmitting therapeutic ultrasound into the brain. As with spinal applications, the array may be used for imaging as well as, or instead of, therapy. This could be used therapeutically for achieving reversible opening of the blood-brain barrier in order to deliver drugs to the nervous system, or diagnostically in order to achieve improved imaging of blood flow during a hemorrhagic or ischaemic stroke event, which could then be treated by transcranial sonothrombolysis.

The invention claimed is:

1. A pressure wave system comprising: a plurality of modules, each module comprising a plurality of pressure wave transducer elements, the transducer elements all being arranged to transmit therapeutic pressure waves at the same transmission frequency;
   at least one connector operable to connect the modules together in each of a plurality of different configurations of the modules whereby the modules can form a reconfigurable transmitter array having a plurality of different shapes each associated with one of the configurations;
   a further pressure wave transducer supported on a needle arranged for insertion into a patient at a target location and arranged to transmit test pressure waves;
   a controller arranged to: determine a received phase offset for the test pressure waves as received at each of the transducer elements; reverse the phase offsets to determine a transmission phase offset for each of the transducer elements; and control the transducer elements to transmit the therapeutic pressure waves at the transmission frequency with the transmission phase offsets such that the therapeutic pressure waves from the transducer elements arrive at the target location in phase with each other; and
   wherein the transducer elements on each of the modules are arranged in a curved array, the curved array of each of the modules having a shape, the shape of the curved array of all of the modules being the same; each of the curved arrays has a length and two ends; each of the curved arrays has a radius of curvature which is constant along its length and the at least one connector is configured such that any two of the modules can be connected end-to-end such that the curved arrays of said two of the modules have a common centre of curvature.

2. The system according to claim 1, wherein each of the curved arrays is part-spherical, and the at least one connector is arranged such that, in each of the configurations, the transducer elements of all of the modules together form a single part-spherical array.

3. The system according to claim 1, wherein each of the modules is of a rectangular shape having two sides and two ends, and the at least one connector is arranged such that two of the modules can be connected together side-to-side or end-to-end.

4. The system according to claim 1, wherein:
   each of the transducer elements is operable to transmit pressure waves and the system further comprises a controller arranged to control the transducer elements on all of the modules;
   the controller is arranged to store configuration data indicative of a current configuration of the modules, and to control the transducer elements using the configuration data thereby to coordinate transmission from the transducer elements; and
   the controller is arranged to identify a target focal point and to coordinate the transducer elements so as to focus transmitted pressure waves at the target focal point.

5. The system according to claim 4, wherein the controller is arranged to vary a timing of transmissions from at least one of the transducer elements relative to a timing of the transmissions from at least another one of the transducer elements thereby to move the focal point of the transmitted pressure waves.

6. The system according to claim 1, wherein each of the transducer elements is arranged to detect pressure waves by generating an output signal in response to receipt of pressure waves; the system further comprises a processor arranged to process the output signals; and the processor is arranged to generate an image from the output signals.

7. The system according to claim 6, wherein the processor is arranged to store configuration data indicative of a current configuration of the modules, and to process the output signals based on the configuration data to generate the image.

8. The system according to claim 1, wherein the further pressure wave transducer is arranged to generate an output signal indicative of a received pressure wave, and the controller is arranged to control the transducer elements in the array to transmit pressure waves in sequence and to analyse the output signal to determine the transmission time between the further pressure wave transducer and each of the array of pressure wave transducer elements.

9. The system according to claim 8, wherein the further pressure wave transducer is supported on a needle arranged for insertion into a patient at a target location, and wherein the needle is a hollow needle arranged to deliver a substance to the target location or extract a substance from the target location.

10. A pressure wave system comprising: a plurality of modules, each module comprising a plurality of pressure wave transducer elements, the transducer elements all being arranged to transmit pressure waves at the same transmission frequency;
    at least one connector operable to connect the modules together in each of a plurality of different configurations of the modules whereby the modules can form a reconfigurable transmitter array having a plurality of different shapes each associated with one of the configurations;
    a further pressure wave transducer supported on a needle arranged for insertion into a patient at a target location and arranged to receive the pressure waves from each of the transducer elements;
    a controller arranged to: determine a transmission time for the pressure waves from each of the transducer elements to the further pressure wave transducer; determine from the transmission time for the pressure waves from each of the transducer elements a respective phase offset; and control the transducer elements to transmit ultrasound at the transmission frequency and with the respective phase offsets such that the pressure waves from the transducer elements arrive at the target location in phase with each other; and wherein the transducer elements on each of the modules are arranged in a curved array, the curved array of each of the modules having a shape, the shape of the curved array of all of the modules being the same; each of the curved arrays has a length and two ends; each of the curved arrays has a radius of curvature which is constant along its length and the at least one connector is configured such that any two of the modules can be connected end-to-end such that the curved arrays of said two of the modules have a common centre of curvature.

11. A pressure wave system comprising: a plurality of modules, each module comprising a plurality of pressure wave transducer elements each arranged to receive pressure waves and output a signal in response thereto;

at least one connector operable to connect the modules together in each of a plurality of different configurations of the modules whereby the modules can form a reconfigurable array having a plurality of different shapes each associated with one of the configurations;

a further pressure wave transducer supported on a needle arranged for insertion into a patient at a target location;

a controller arranged to: analyse a transmission time of a pressure wave test signal transmitted between each of the array of pressure wave transducer elements and the further ultrasound transducer; and process signals from the array of transducer elements to generate an image of the target location using an imaging algorithm, wherein the imaging algorithm is adjusted based on the transmission times of the pressure wave test signal; and wherein the transducer elements on each of the modules are arranged in a curved array, the curved array of each of the modules having a shape, the shape of the curved array of all of the modules being the same; each of the curved arrays has a length and two ends; each of the curved arrays has a radius of curvature which is constant along its length and the at least one connector is configured such that any two of the modules can be connected end-to-end such that the curved arrays of said two of the modules have a common centre of curvature.

* * * * *